US008560250B2

(12) United States Patent　　(10) Patent No.: US 8,560,250 B2
　Connolly et al.　　(45) Date of Patent: ＊Oct. 15, 2013

(54) METHOD AND SYSTEM FOR TRANSFERRING ANALYTE TEST DATA

(75) Inventors: Brian Edmond Connolly, Reading, MA (US); Chad Harold Mace, Hudson, NH (US); Marc R. Lai, Dover, MA (US)

(73) Assignee: Abbott Laboratories, Abbott Park, IL (US)

( * ) Notice: Subject to any disclaimer, the term of this patent is extended or adjusted under 35 U.S.C. 154(b) by 225 days.

This patent is subject to a terminal disclaimer.

(21) Appl. No.: 12/859,072

(22) Filed: Aug. 18, 2010

(65) Prior Publication Data

US 2010/0309001 A1　　Dec. 9, 2010

Related U.S. Application Data

(63) Continuation of application No. 12/549,296, filed on Aug. 27, 2009, which is a continuation of application No. 10/407,695, filed on Apr. 4, 2003, now Pat. No. 7,587,287.

(51) Int. Cl.
　*G01N 31/00*　　(2006.01)
(52) U.S. Cl.
　USPC ........................................................... 702/32
(58) Field of Classification Search
　USPC .................. 702/32, 122; 600/300; 422/82.01
　See application file for complete search history.

(56) References Cited

U.S. PATENT DOCUMENTS

| | | | |
|---|---|---|---|
| 3,304,413 A | 2/1967 | Lehmann | |
| 3,651,318 A | 3/1972 | Czekajewski | |
| 3,698,386 A | 10/1972 | Fried | |
| 3,768,014 A | 10/1973 | Smith | |
| 3,919,051 A | 11/1975 | Koch | |

(Continued)

FOREIGN PATENT DOCUMENTS

| | | |
|---|---|---|
| CA | 2143172 | 7/2005 |
| CA | 2396613 | 3/2008 |

(Continued)

OTHER PUBLICATIONS

Abstract of Japanese Publication No. JP-2002-185450, Published Jun. 28, 2002.

(Continued)

*Primary Examiner* — Tung S Lau
*Assistant Examiner* — Xiuquin Sun
(74) *Attorney, Agent, or Firm* — Edward J. Baba; Bozicevic, Field & Francis LLP

(57) ABSTRACT

A system for transferring data includes an analyte test instrument (ATI) adapted to store data, a wirelessly enabled data management device (DMD) for comprehensively analyzing data, and an adaptor removably connected to the ATI for transferring data stored on the ATI to the DMD. The adaptor includes a data communication device capable of removable connection with the ATI, a microprocessor electrically connected to the data communication device, a wireless controller electrically connected to the microprocessor and a wireless transceiver electrically connected to the wireless controller. In use, data transfer is executed between the ATI and the DMD by electrically and mechanically connecting the adaptor to the ATI. Data stored on the ATI is then automatically downloaded into adaptor memory. Upon completion of the download, the user activates an externally accessible input device on the adaptor which, in turn, wirelessly transmits data from the adaptor memory to the DMD.

24 Claims, 7 Drawing Sheets

(56) References Cited

U.S. PATENT DOCUMENTS

| | | |
|---|---|---|
| 4,003,379 A | 1/1977 | Ellinwood, Jr. |
| 4,021,718 A | 5/1977 | Konrad |
| 4,154,231 A | 5/1979 | Russell |
| 4,193,026 A | 3/1980 | Finger et al. |
| 4,240,889 A | 12/1980 | Yoda |
| 4,271,449 A | 6/1981 | Grogan |
| 4,318,784 A | 3/1982 | Higgins |
| 4,331,869 A | 5/1982 | Rollo |
| 4,392,933 A | 7/1983 | Nakamura |
| 4,397,956 A | 8/1983 | Maggio |
| 4,407,959 A | 10/1983 | Tsuji |
| 4,417,588 A | 11/1983 | Houghton |
| 4,420,564 A | 12/1983 | Tsuji |
| 4,444,892 A | 4/1984 | Malmros |
| 4,475,901 A | 10/1984 | Kraegen et al. |
| 4,483,924 A | 11/1984 | Tsuji |
| 4,569,589 A | 2/1986 | Neufeld |
| 4,595,479 A | 6/1986 | Kimura |
| 4,601,707 A | 7/1986 | Albisser et al. |
| 4,633,881 A | 1/1987 | Moore |
| 4,648,408 A | 3/1987 | Hutcheson |
| 4,653,513 A | 3/1987 | Dombrowski |
| 4,674,652 A | 6/1987 | Aten |
| 4,685,903 A | 8/1987 | Cable et al. |
| 4,686,624 A | 8/1987 | Blum |
| 4,703,324 A | 10/1987 | White |
| 4,731,726 A | 3/1988 | Allen, III |
| 4,750,496 A | 6/1988 | Reinhart |
| 4,803,625 A | 2/1989 | Fu |
| 4,835,372 A | 5/1989 | Gombrich |
| RE32,947 E | 6/1989 | Dormer et al. |
| RE32,974 E | 7/1989 | Porat |
| 4,857,713 A | 8/1989 | Brown |
| 4,858,617 A | 8/1989 | Sanders |
| 4,870,561 A | 9/1989 | Love |
| 4,874,499 A | 10/1989 | Smith |
| 4,899,839 A | 2/1990 | Dessertine |
| 4,920,969 A | 5/1990 | Suzuki |
| 4,920,977 A | 5/1990 | Hasynes |
| 4,936,956 A | 6/1990 | Wrighton |
| 4,942,127 A | 7/1990 | Wada |
| 4,945,045 A | 7/1990 | Forrest |
| 4,957,115 A | 9/1990 | Selker |
| 4,958,632 A | 9/1990 | Duggan |
| 4,968,400 A | 11/1990 | Shimomura |
| 4,994,068 A | 2/1991 | Hufnagle |
| 5,007,427 A | 4/1991 | Suzuki |
| 5,016,172 A | 5/1991 | Dessertine |
| 5,019,974 A | 5/1991 | Beckers |
| 5,034,192 A | 7/1991 | Wrighton |
| 5,037,527 A | 8/1991 | Hayashi |
| 5,049,487 A | 9/1991 | Phillips |
| 5,051,688 A | 9/1991 | Murase et al. |
| 5,068,536 A | 11/1991 | Rosenthal |
| 5,073,500 A | 12/1991 | Saito |
| 5,075,792 A | 12/1991 | Brown |
| 5,077,476 A | 12/1991 | Rosenthal |
| 5,078,854 A | 1/1992 | Burgess |
| 5,084,828 A | 1/1992 | Kaufman |
| 5,094,951 A | 3/1992 | Rosenberg |
| 5,096,560 A | 3/1992 | Takai |
| 5,096,836 A | 3/1992 | Macho |
| 5,097,834 A | 3/1992 | Skrabal |
| 5,111,539 A | 5/1992 | Hiruta |
| 5,111,818 A | 5/1992 | Suzuki |
| 5,114,678 A | 5/1992 | Crawford |
| 5,120,421 A | 6/1992 | Glass |
| 5,124,661 A | 6/1992 | Zelin et al. |
| 5,126,247 A | 6/1992 | Palmer |
| 5,130,009 A | 7/1992 | Marsoner |
| 5,134,391 A | 7/1992 | Okada |
| 5,140,393 A | 8/1992 | Hijikihigawa |
| 5,168,046 A | 12/1992 | Hamamoto |
| 5,182,707 A | 1/1993 | Cooper |
| 5,184,359 A | 2/1993 | Tsukamura |
| 5,185,256 A | 2/1993 | Nankai |
| 5,190,041 A | 3/1993 | Palti |
| 5,192,415 A | 3/1993 | Yoshioka |
| 5,200,051 A | 4/1993 | Cozzette |
| 5,204,532 A | 4/1993 | Rosenthal |
| 5,206,145 A | 4/1993 | Cattell |
| 5,216,597 A | 6/1993 | Beckers |
| 5,227,042 A | 7/1993 | Zawodzinski |
| 5,236,143 A | 8/1993 | Dragon |
| 5,237,993 A | 8/1993 | Skrabal |
| 5,245,314 A | 9/1993 | Kah |
| 5,251,126 A | 10/1993 | Kahn |
| 5,261,401 A | 11/1993 | Baker |
| 5,265,888 A | 11/1993 | Yamamoto |
| 5,266,179 A | 11/1993 | Nankai |
| 5,269,212 A | 12/1993 | Peters |
| 5,272,060 A | 12/1993 | Hamamoto |
| 5,275,159 A | 1/1994 | Griebel |
| 5,278,079 A | 1/1994 | Gubinski |
| 5,279,294 A | 1/1994 | Anderson |
| 5,282,950 A | 2/1994 | Dietze |
| 5,289,497 A | 2/1994 | Jackobson et al. |
| 5,304,468 A | 4/1994 | Phillips |
| 5,307,263 A | 4/1994 | Brown |
| 5,309,919 A | 5/1994 | Snell |
| 5,310,885 A | 5/1994 | Maier |
| 5,317,691 A | 5/1994 | Traeger |
| 5,324,303 A | 6/1994 | Strong |
| 5,326,449 A | 7/1994 | Cunningham |
| 5,333,615 A | 8/1994 | Craelius et al. |
| 5,337,258 A | 8/1994 | Dennis |
| 5,342,408 A | 8/1994 | deCoriolis et al. |
| 5,358,135 A | 10/1994 | Robbins et al. |
| 5,364,797 A | 11/1994 | Olson |
| 5,366,609 A | 11/1994 | White |
| 5,371,734 A | 12/1994 | Fischer |
| 5,376,251 A | 12/1994 | Kaneko |
| 5,377,258 A | 12/1994 | Bro |
| 5,380,422 A | 1/1995 | Negishi |
| 5,382,346 A | 1/1995 | Uenoyama |
| 5,393,903 A | 2/1995 | Gratzel |
| 5,400,794 A | 3/1995 | Gorman |
| 5,410,326 A | 4/1995 | Goldstein |
| 5,410,471 A | 4/1995 | Alyfuku |
| 5,410,474 A | 4/1995 | Fox |
| 5,413,690 A | 5/1995 | Kost |
| 5,417,222 A | 5/1995 | Dempsey |
| 5,422,246 A | 6/1995 | Koopal |
| 5,431,691 A | 7/1995 | Snell |
| 5,437,973 A | 8/1995 | Vadgama |
| 5,440,559 A | 8/1995 | Gaskill |
| 5,456,692 A | 10/1995 | Smith, Jr. |
| 5,484,991 A | 1/1996 | Sherman |
| 5,487,751 A | 1/1996 | Radons |
| 5,499,243 A | 3/1996 | Hall |
| 5,501,956 A | 3/1996 | Wada |
| 5,507,288 A | 4/1996 | Bocker |
| 5,508,171 A | 4/1996 | Walling |
| 5,514,253 A | 5/1996 | Davis |
| 5,518,006 A | 5/1996 | Mawhirt |
| 5,519,527 A | 5/1996 | Panton |
| 5,520,787 A | 5/1996 | Hanagan |
| 5,525,511 A | 6/1996 | D'Costa |
| 5,526,120 A | 6/1996 | Jina |
| 5,528,391 A | 6/1996 | Elrod |
| 5,532,686 A | 7/1996 | Urbas et al. |
| 5,544,196 A | 8/1996 | Tiedmann, Jr. et al. |
| 5,549,113 A | 8/1996 | Halleck |
| 5,549,115 A | 8/1996 | Morgan |
| 5,552,027 A | 9/1996 | Birkle |
| 5,554,166 A | 9/1996 | Lange |
| 5,556,524 A | 9/1996 | Albers |
| 5,560,357 A | 10/1996 | Faupel |
| 5,566,022 A | 10/1996 | Segev |
| 5,569,212 A | 10/1996 | Brown |
| 5,575,895 A | 11/1996 | Ikeda |
| 5,580,527 A | 12/1996 | Bell |
| 5,580,794 A | 12/1996 | Allen |
| 5,581,206 A | 12/1996 | Chevallier et al. |

(56) References Cited

U.S. PATENT DOCUMENTS

| | | |
|---|---|---|
| 5,596,994 A | 1/1997 | Bro |
| 5,600,301 A | 2/1997 | Robinson, III |
| 5,601,435 A | 2/1997 | Quy |
| 5,623,925 A | 4/1997 | Swenson |
| 5,623,933 A | 4/1997 | Amano et al. |
| 5,628,309 A | 5/1997 | Brown |
| 5,629,981 A | 5/1997 | Nerlikar |
| 5,634,468 A | 6/1997 | Platt et al. |
| 5,636,264 A | 6/1997 | Sulavuori |
| 5,643,212 A | 7/1997 | Coutre |
| 5,650,062 A | 7/1997 | Ikeda |
| 5,659,454 A | 8/1997 | Vermesse |
| 5,678,571 A | 10/1997 | Brown |
| 5,682,157 A | 10/1997 | Asmussen |
| 5,686,717 A | 11/1997 | Knowles |
| 5,695,949 A | 12/1997 | Galen |
| 5,701,894 A | 12/1997 | Cherry |
| 5,704,922 A | 1/1998 | Brown |
| 5,710,630 A | 1/1998 | Essenpreis |
| 5,720,733 A | 2/1998 | Brown |
| 5,720,862 A | 2/1998 | Hamamoto |
| 5,721,783 A | 2/1998 | Anderson |
| 5,724,030 A | 3/1998 | Urbas et al. |
| 5,724,168 A | 3/1998 | Oschmann |
| 5,727,548 A | 3/1998 | Hill |
| 5,730,124 A | 3/1998 | Yamauchi |
| 5,730,654 A | 3/1998 | Brown |
| 5,735,273 A | 4/1998 | Kurnik et al. |
| 5,735,285 A | 4/1998 | Albert |
| 5,741,688 A | 4/1998 | Oxenbøll |
| 5,746,217 A | 5/1998 | Erickson |
| 5,748,103 A | 5/1998 | Flach et al. |
| 5,749,907 A | 5/1998 | Mann |
| 5,757,277 A | 5/1998 | Kobayashi |
| 5,758,290 A | 5/1998 | Nealon et al. |
| 5,770,028 A | 6/1998 | Maley |
| 5,772,586 A | 6/1998 | Heinonen |
| 5,781,321 A | 7/1998 | Kobayashi |
| 5,782,814 A | 7/1998 | Brown |
| 5,786,584 A | 7/1998 | Button |
| 5,792,117 A | 8/1998 | Brown |
| 5,793,292 A | 8/1998 | Ivey |
| 5,804,047 A | 9/1998 | Karube et al. |
| 5,804,048 A | 9/1998 | Wong |
| 5,820,570 A | 10/1998 | Erickson |
| 5,827,179 A | 10/1998 | Lichter |
| 5,828,943 A | 10/1998 | Brown |
| 5,830,064 A | 11/1998 | Bradish et al. |
| 5,830,341 A | 11/1998 | Gilmartin |
| 5,832,448 A | 11/1998 | Brown |
| 5,833,603 A | 11/1998 | Kovacs et al. |
| 5,834,224 A | 11/1998 | Ruger |
| 5,837,454 A | 11/1998 | Cozzette |
| 5,837,546 A | 11/1998 | Allen |
| 5,840,020 A | 11/1998 | Heinonen |
| 5,846,702 A | 12/1998 | Deng |
| 5,846,744 A | 12/1998 | Athey |
| 5,857,967 A | 1/1999 | Frid |
| 5,857,983 A | 1/1999 | Douglas |
| 5,860,917 A | 1/1999 | Comanor |
| 5,861,968 A | 1/1999 | Kerklaan |
| 5,872,713 A | 2/1999 | Douglas |
| 5,873,990 A | 2/1999 | Wojciechowski |
| 5,877,880 A | 3/1999 | Kuo |
| 5,879,163 A | 3/1999 | Brown |
| 5,879,311 A | 3/1999 | Duchon |
| 5,880,829 A | 3/1999 | Kauhaniemi |
| 5,887,133 A | 3/1999 | Brown |
| 5,891,049 A | 4/1999 | Cyrus et al. |
| 5,897,493 A | 4/1999 | Brown |
| 5,899,855 A | 5/1999 | Brown |
| 5,903,373 A | 5/1999 | Welch |
| 5,903,374 A | 5/1999 | Kobayashi |
| 5,913,310 A | 6/1999 | Brown |
| 5,918,603 A | 7/1999 | Brown |
| 5,925,021 A | 7/1999 | Castellano |
| 5,929,771 A | 7/1999 | Gaskill |
| 5,931,791 A | 8/1999 | Saltzstein |
| 5,933,136 A | 8/1999 | Brown |
| 5,935,099 A | 8/1999 | Petterson |
| 5,940,801 A | 8/1999 | Brown |
| 5,942,979 A | 8/1999 | Luppino |
| 5,945,345 A | 8/1999 | Blatt |
| 5,950,632 A | 9/1999 | Reber |
| 5,951,300 A | 9/1999 | Brown |
| 5,951,485 A | 9/1999 | Cyrus et al. |
| 5,951,492 A | 9/1999 | Douglas |
| 5,956,501 A | 9/1999 | Brown |
| 5,960,403 A | 9/1999 | Brown |
| 5,961,451 A | 10/1999 | Reber |
| 5,968,839 A | 10/1999 | Blatt |
| 5,971,941 A | 10/1999 | Simons |
| 5,974,124 A | 10/1999 | Schlueter, Jr. |
| 5,977,476 A | 11/1999 | Guha |
| 5,981,294 A | 11/1999 | Blatt |
| 5,986,787 A | 11/1999 | Ohshima |
| 5,994,476 A | 11/1999 | Shin |
| 5,997,476 A | 12/1999 | Brown |
| 6,004,441 A | 12/1999 | Fujiwara |
| 6,024,699 A | 2/2000 | Surwit |
| 6,027,459 A | 2/2000 | Shain |
| 6,027,692 A | 2/2000 | Galen |
| 6,032,199 A | 2/2000 | Lim |
| 6,033,866 A | 3/2000 | Guo |
| 6,052,565 A | 4/2000 | Ishikura et al. |
| D424,696 S | 5/2000 | Ray |
| 6,063,459 A | 5/2000 | Velte |
| 6,066,243 A | 5/2000 | Anderson |
| 6,068,615 A | 5/2000 | Brown |
| D426,638 S | 6/2000 | Ray |
| D427,312 S | 6/2000 | Douglas |
| 6,071,249 A | 6/2000 | Cunningham |
| 6,071,251 A | 6/2000 | Cunningham |
| 6,071,294 A | 6/2000 | Simons |
| 6,071,391 A | 6/2000 | Gotoh |
| 6,088,730 A | 7/2000 | Kato |
| 6,091,987 A | 7/2000 | Thompson |
| 6,093,156 A | 7/2000 | Cunningham |
| 6,097,480 A | 8/2000 | Kaplan |
| 6,097,831 A | 8/2000 | Wieck |
| 6,099,484 A | 8/2000 | Douglas |
| 6,101,478 A | 8/2000 | Brown |
| 6,103,033 A | 8/2000 | Say |
| 6,106,780 A | 8/2000 | Douglas |
| 6,110,148 A | 8/2000 | Brown |
| 6,113,578 A | 9/2000 | Brown |
| 6,115,161 A | 9/2000 | Cho |
| 6,120,676 A | 9/2000 | Heller |
| 6,122,351 A | 9/2000 | Schlueter, Jr. |
| 6,124,134 A | 9/2000 | Stark |
| 6,130,623 A | 10/2000 | MacLellan et al. |
| 6,134,504 A | 10/2000 | Douglas |
| 6,143,164 A | 11/2000 | Heller |
| 6,144,837 A | 11/2000 | Quy |
| 6,144,871 A | 11/2000 | Saito et al. |
| 6,144,922 A | 11/2000 | Douglas |
| 6,148,094 A | 11/2000 | Kinsella |
| 6,151,586 A | 11/2000 | Brown |
| 6,153,062 A | 11/2000 | Saito |
| 6,153,069 A | 11/2000 | Pottgen |
| 6,159,147 A | 12/2000 | Lichter |
| 6,161,095 A | 12/2000 | Brown |
| 6,162,639 A | 12/2000 | Douglas |
| 6,167,362 A | 12/2000 | Brown |
| 6,168,563 B1 | 1/2001 | Brown |
| 6,170,318 B1 | 1/2001 | Lewis |
| 6,175,752 B1 | 1/2001 | Say |
| 6,186,145 B1 | 2/2001 | Brown |
| 6,192,891 B1 | 2/2001 | Gravel |
| 6,193,873 B1 | 2/2001 | Ohara |
| D439,242 S | 3/2001 | Brown |
| 6,196,970 B1 | 3/2001 | Brown |
| 6,198,957 B1 | 3/2001 | Green |
| 6,200,265 B1 | 3/2001 | Walsh et al. |

(56) References Cited

U.S. PATENT DOCUMENTS

| | | |
|---|---|---|
| 6,203,495 B1 | 3/2001 | Bardy et al. |
| 6,206,841 B1 | 3/2001 | Cunningham |
| 6,210,272 B1 | 4/2001 | Brown |
| 6,219,565 B1 | 4/2001 | Cupp |
| 6,233,539 B1 | 5/2001 | Brown |
| 6,236,486 B1 | 5/2001 | Nocker, IV |
| 6,241,862 B1 | 6/2001 | McAleer |
| 6,246,330 B1 | 6/2001 | Nielsen |
| 6,246,992 B1 | 6/2001 | Brown |
| 6,248,065 B1 | 6/2001 | Brown |
| 6,248,067 B1 | 6/2001 | Causey, III |
| 6,251,260 B1 | 6/2001 | Heller |
| 6,256,129 B1 | 7/2001 | Kim |
| 6,256,643 B1 | 7/2001 | Cork |
| 6,260,022 B1 | 7/2001 | Brown |
| 6,266,645 B1 | 7/2001 | Simpson |
| 6,270,445 B1 | 8/2001 | Dean, Jr. |
| 6,281,006 B1 | 8/2001 | Heller |
| 6,281,999 B1 | 8/2001 | Watson |
| 6,291,200 B1 | 9/2001 | LeJeune et al. |
| 6,294,281 B1 | 9/2001 | Heller |
| 6,294,997 B1 | 9/2001 | Paratore et al. |
| 6,295,506 B1 | 9/2001 | Heinonen |
| 6,299,757 B1 | 10/2001 | Feldman |
| 6,301,035 B1 | 10/2001 | Schairer |
| 6,307,867 B1 | 10/2001 | Roobol et al. |
| 6,313,749 B1 | 11/2001 | Horne et al. |
| 6,329,161 B1 | 12/2001 | Heller |
| 6,330,426 B2 | 12/2001 | Brown |
| 6,334,778 B1 | 1/2002 | Brown |
| 6,338,790 B1 | 1/2002 | Feldman |
| 6,377,894 B1 | 4/2002 | Deweese |
| 6,379,301 B1 | 4/2002 | Worthington |
| 6,400,974 B1 | 6/2002 | Lesho |
| 6,418,346 B1 | 7/2002 | Nelson et al. |
| 6,442,637 B1 | 8/2002 | Hawkins |
| 6,442,639 B1 | 8/2002 | McElhattan |
| 6,442,672 B1 | 8/2002 | Ganapathy |
| 6,449,075 B1 | 9/2002 | Watson |
| 6,482,156 B2 | 11/2002 | Iliff |
| 6,494,830 B1 | 12/2002 | Wessel |
| 6,496,729 B2 | 12/2002 | Thompson |
| 6,497,655 B1 | 12/2002 | Linberg et al. |
| 6,505,121 B1 | 1/2003 | Russel |
| 6,516,359 B1 | 2/2003 | Kurihara |
| 6,541,266 B2 | 4/2003 | Modzelweskei et al. |
| 6,549,796 B2 | 4/2003 | Sohrab |
| 6,558,320 B1 | 5/2003 | Causey, III |
| 6,558,321 B1 | 5/2003 | Burd et al. |
| 6,561,975 B1 | 5/2003 | Pool et al. |
| 6,574,510 B2 | 6/2003 | Von Arx et al. |
| 6,579,231 B1 | 6/2003 | Phipps |
| 6,607,509 B2 | 8/2003 | Bobroff et al. |
| 6,608,562 B1 | 8/2003 | Kimura et al. |
| 6,610,012 B2 | 8/2003 | Mault |
| 6,611,206 B2 | 8/2003 | Eshelman et al. |
| 6,616,613 B1 | 9/2003 | Goodman |
| 6,627,154 B1 | 9/2003 | Goodman et al. |
| 6,633,772 B2 | 10/2003 | Ford |
| 6,635,167 B1 | 10/2003 | Batman et al. |
| 6,641,533 B2 * | 11/2003 | Causey et al. ................. 600/300 |
| 6,694,191 B2 | 2/2004 | Starkweather et al. |
| 6,701,270 B1 | 3/2004 | Miller et al. |
| 6,702,857 B2 | 3/2004 | Brauker et al. |
| 6,708,057 B2 | 3/2004 | Morganroth |
| 6,731,976 B2 | 5/2004 | Penn et al. |
| 6,735,183 B2 | 5/2004 | O'Toole et al. |
| 6,735,479 B2 | 5/2004 | Fabian et al. |
| 6,736,797 B1 | 5/2004 | Larsen et al. |
| 6,741,877 B1 | 5/2004 | Shults et al. |
| 6,748,445 B1 | 6/2004 | Darcey et al. |
| 6,780,156 B2 | 8/2004 | Haueter et al. |
| 6,790,178 B1 | 9/2004 | Mault |
| 6,804,558 B2 | 10/2004 | Haller et al. |
| 6,810,309 B2 | 10/2004 | Sadler et al. |
| RE38,681 E | 1/2005 | Kurnik et al. |
| 6,849,237 B2 * | 2/2005 | Housefield et al. ........ 422/82.01 |
| 6,852,104 B2 | 2/2005 | Blomquist |
| 6,862,465 B2 | 3/2005 | Shults et al. |
| 6,878,112 B2 | 4/2005 | Linberg et al. |
| 6,889,331 B2 | 5/2005 | Soerensen et al. |
| 6,902,207 B2 | 6/2005 | Lickliter |
| RE38,775 E | 8/2005 | Kurnik et al. |
| 6,923,764 B2 | 8/2005 | Aceti et al. |
| 6,931,327 B2 | 8/2005 | Goode, Jr. et al. |
| 6,937,222 B2 | 8/2005 | Numao |
| 6,940,403 B2 | 9/2005 | Kail, IV |
| 6,941,163 B2 | 9/2005 | Ford et al. |
| 6,968,294 B2 | 11/2005 | Gutta |
| 6,985,870 B2 | 1/2006 | Martucci et al. |
| 7,009,511 B2 | 3/2006 | Mazar et al. |
| 7,020,508 B2 | 3/2006 | Stivoric et al. |
| 7,041,468 B2 | 5/2006 | Drucker |
| 7,043,305 B2 | 5/2006 | KenKnight et al. |
| 7,052,251 B2 | 5/2006 | Nason et al. |
| 7,058,453 B2 | 6/2006 | Nelson et al. |
| 7,060,030 B2 | 6/2006 | Von Arx et al. |
| 7,060,031 B2 | 6/2006 | Webb et al. |
| 7,074,307 B2 | 7/2006 | Simpson et al. |
| 7,081,195 B2 | 7/2006 | Simpson et al. |
| 7,082,334 B2 | 7/2006 | Boute et al. |
| 7,089,780 B2 | 8/2006 | Sunshine et al. |
| 7,108,778 B2 | 9/2006 | Simpson et al. |
| 7,110,803 B2 | 9/2006 | Shults et al. |
| 7,114,502 B2 | 10/2006 | Schulman et al. |
| 7,124,027 B1 | 10/2006 | Ernst et al. |
| 7,125,382 B2 | 10/2006 | Zhou et al. |
| 7,134,999 B2 | 11/2006 | Brauker et al. |
| 7,136,689 B2 | 11/2006 | Shults et al. |
| 7,154,398 B2 | 12/2006 | Chen et al. |
| 7,155,112 B2 | 12/2006 | Uno et al. |
| 7,155,290 B2 | 12/2006 | Von Arx et al. |
| 7,192,450 B2 | 3/2007 | Brauker et al. |
| 7,203,549 B2 | 4/2007 | Schommer et al. |
| 7,207,974 B2 | 4/2007 | Safabash et al. |
| 7,221,977 B1 | 5/2007 | Weaver et al. |
| 7,226,442 B2 | 6/2007 | Sheppard et al. |
| 7,226,978 B2 | 6/2007 | Tapsak et al. |
| 7,228,162 B2 | 6/2007 | Ward et al. |
| 7,228,182 B2 | 6/2007 | Healy et al. |
| 7,237,712 B2 | 7/2007 | DeRocco et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,291,107 B2 | 11/2007 | Hellwig et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,324,850 B2 | 1/2008 | Persen et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,398,183 B2 | 7/2008 | Holland et al. |
| 7,399,277 B2 | 7/2008 | Saidara et al. |
| 7,408,132 B2 | 8/2008 | Wambsganss et al. |
| 7,419,573 B2 | 9/2008 | Gundel |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,565,197 B2 | 7/2009 | Haubrich et al. |
| 7,574,266 B2 | 8/2009 | Dudding et al. |
| 7,583,990 B2 | 9/2009 | Goode, Jr. et al. |
| 7,587,287 B2 * | 9/2009 | Connolly et al. ................ 702/32 |
| 7,591,801 B2 | 9/2009 | Brauker et al. |
| 7,599,726 B2 | 10/2009 | Goode, Jr. et al. |
| 7,602,310 B2 | 10/2009 | Mann et al. |

(56) References Cited

U.S. PATENT DOCUMENTS

| | | |
|---|---|---|
| 7,604,178 B2 | 10/2009 | Stewart |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,668,596 B2 | 2/2010 | Von Arx et al. |
| 7,701,052 B2 | 4/2010 | Borland et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,771,352 B2 | 8/2010 | Shults et al. |
| 7,774,145 B2 | 8/2010 | Brauker et al. |
| 7,778,680 B2 | 8/2010 | Goode, Jr. et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,813,809 B2 | 10/2010 | Strother et al. |
| 7,826,981 B2 | 11/2010 | Goode, Jr. et al. |
| 7,831,310 B2 | 11/2010 | Lebel et al. |
| 7,860,574 B2 | 12/2010 | Von Arx et al. |
| 7,882,611 B2 | 2/2011 | Shah et al. |
| 7,899,511 B2 | 3/2011 | Shults et al. |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,955,258 B2 | 6/2011 | Goscha et al. |
| 7,970,448 B2 | 6/2011 | Shults et al. |
| 7,974,672 B2 | 7/2011 | Shults et al. |
| 7,999,674 B2 | 8/2011 | Kamen |
| 2001/0016310 A1 | 8/2001 | Brown |
| 2001/0032278 A1 | 10/2001 | Brown |
| 2001/0037366 A1 | 11/2001 | Webb et al. |
| 2001/0047125 A1 | 11/2001 | Quy |
| 2001/0047127 A1 | 11/2001 | New et al. |
| 2001/0049096 A1 | 12/2001 | Brown |
| 2002/0013522 A1 | 1/2002 | Lav et al. |
| 2002/0013538 A1 | 1/2002 | Teller |
| 2002/0016530 A1 | 2/2002 | Brown |
| 2002/0016719 A1 | 2/2002 | Nemeth et al. |
| 2002/0019584 A1 | 2/2002 | Schulze et al. |
| 2002/0019748 A1 | 2/2002 | Brown |
| 2002/0049482 A1 | 4/2002 | Fabian et al. |
| 2002/0063060 A1 | 5/2002 | Gascoyne |
| 2002/0072784 A1 | 6/2002 | Sheppard et al. |
| 2002/0074162 A1 | 6/2002 | Su et al. |
| 2002/0081559 A1 | 6/2002 | Brown |
| 2002/0082797 A1* | 6/2002 | Deweese et al. .............. 702/122 |
| 2002/0083461 A1 | 6/2002 | Hutcheson |
| 2002/0084196 A1 | 7/2002 | Liamos et al. |
| 2002/0091796 A1 | 7/2002 | Higginson et al. |
| 2002/0093969 A1 | 7/2002 | Lin et al. |
| 2002/0118528 A1 | 8/2002 | Su et al. |
| 2002/0126036 A1 | 9/2002 | Flaherty et al. |
| 2002/0147135 A1 | 10/2002 | Schnell |
| 2003/0023317 A1 | 1/2003 | Brauker et al. |
| 2003/0032874 A1 | 2/2003 | Rhodes et al. |
| 2003/0050537 A1 | 3/2003 | Wessel |
| 2003/0072424 A1 | 4/2003 | Evans |
| 2003/0076792 A1 | 4/2003 | Theimer |
| 2003/0081370 A1 | 5/2003 | Haskell et al. |
| 2003/0083114 A1 | 5/2003 | Lavin |
| 2003/0114897 A1 | 6/2003 | Von Arx et al. |
| 2003/0122021 A1 | 7/2003 | McConnell et al. |
| 2003/0144579 A1 | 7/2003 | Buss |
| 2003/0146841 A1 | 8/2003 | Koenig |
| 2003/0176183 A1 | 9/2003 | Drucker |
| 2003/0204290 A1 | 10/2003 | Sadler et al. |
| 2003/0208114 A1 | 11/2003 | Ackerman |
| 2003/0212579 A1 | 11/2003 | Brown et al. |
| 2003/0217966 A1 | 11/2003 | Tapsak et al. |
| 2004/0011671 A1 | 1/2004 | Shults et al. |
| 2004/0017300 A1 | 1/2004 | Kotzin et al. |
| 2004/0030226 A1 | 2/2004 | Quy |
| 2004/0030531 A1 | 2/2004 | Miller et al. |
| 2004/0045879 A1 | 3/2004 | Shults et al. |
| 2004/0100376 A1 | 5/2004 | Lye et al. |
| 2004/0105411 A1 | 6/2004 | Boatwright et al. |
| 2004/0122530 A1 | 6/2004 | Hansen et al. |
| 2004/0138588 A1 | 7/2004 | Saikley |
| 2004/0152961 A1 | 8/2004 | Carlson et al. |
| 2004/0167464 A1 | 8/2004 | Ireland et al. |
| 2004/0186362 A1 | 9/2004 | Brauker et al. |
| 2004/0199059 A1 | 10/2004 | Brauker et al. |
| 2004/0221057 A1 | 11/2004 | Darcey et al. |
| 2004/0235446 A1 | 11/2004 | Flaherty et al. |
| 2005/0019848 A1 | 1/2005 | Lee |
| 2005/0031689 A1 | 2/2005 | Shults et al. |
| 2005/0043598 A1 | 2/2005 | Goode, Jr. et al. |
| 2005/0090607 A1 | 4/2005 | Tapsak et al. |
| 2005/0112169 A1 | 5/2005 | Brauker et al. |
| 2005/0112544 A1 | 5/2005 | Xu et al. |
| 2005/0113886 A1 | 5/2005 | Fischell et al. |
| 2005/0143635 A1 | 6/2005 | Kamath et al. |
| 2005/0176136 A1 | 8/2005 | Burd et al. |
| 2005/0187720 A1 | 8/2005 | Goode, Jr. et al. |
| 2005/0192557 A1 | 9/2005 | Brauker et al. |
| 2005/0203349 A1 | 9/2005 | Nanikashvili |
| 2005/0204134 A1 | 9/2005 | Von Arx et al. |
| 2005/0239156 A1 | 10/2005 | Drucker |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0277164 A1 | 12/2005 | Drucker |
| 2006/0015020 A1 | 1/2006 | Neale et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0129733 A1 | 6/2006 | Solbelman |
| 2006/0142651 A1 | 6/2006 | Brister et al. |
| 2006/0200112 A1 | 9/2006 | Paul |
| 2006/0202805 A1 | 9/2006 | Schulman et al. |
| 2006/0202859 A1 | 9/2006 | Mastrototaro et al. |
| 2006/0222566 A1 | 10/2006 | Brauker et al. |
| 2006/0247710 A1 | 11/2006 | Goetz et al. |
| 2006/0287691 A1 | 12/2006 | Drew |
| 2007/0016381 A1 | 1/2007 | Kamath et al. |
| 2007/0055799 A1 | 3/2007 | Koehler et al. |
| 2007/0090511 A1 | 4/2007 | Borland et al. |
| 2007/0156033 A1 | 7/2007 | Causey, III et al. |
| 2007/0163880 A1 | 7/2007 | Woo et al. |
| 2007/0203966 A1 | 8/2007 | Brauker et al. |
| 2007/0232880 A1 | 10/2007 | Siddiqui et al. |
| 2007/0235331 A1 | 10/2007 | Simpson et al. |
| 2007/0244383 A1 | 10/2007 | Talbot et al. |
| 2007/0253021 A1 | 11/2007 | Mehta et al. |
| 2007/0255531 A1 | 11/2007 | Drew |
| 2007/0258395 A1 | 11/2007 | Jollota et al. |
| 2007/0270672 A1 | 11/2007 | Hayter |
| 2007/0285238 A1 | 12/2007 | Batra |
| 2007/0299617 A1 | 12/2007 | Willis |
| 2008/0009304 A1 | 1/2008 | Fry |
| 2008/0018433 A1 | 1/2008 | Pitt-Pladdy |
| 2008/0021666 A1 | 1/2008 | Goode, Jr. et al. |
| 2008/0030369 A1 | 2/2008 | Mann et al. |
| 2008/0033254 A1 | 2/2008 | Kamath et al. |

(56) References Cited

U.S. PATENT DOCUMENTS

| | | |
|---|---|---|
| 2008/0045824 A1 | 2/2008 | Tapsak et al. |
| 2008/0055070 A1 | 3/2008 | Bange et al. |
| 2008/0064943 A1 | 3/2008 | Talbot et al. |
| 2008/0071156 A1 | 3/2008 | Brister et al. |
| 2008/0071328 A1 | 3/2008 | Haubrich et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0108942 A1 | 5/2008 | Brister et al. |
| 2008/0119705 A1 | 5/2008 | Patel et al. |
| 2008/0139910 A1 | 6/2008 | Mastrototaro et al. |
| 2008/0167572 A1 | 7/2008 | Stivoric et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0235469 A1 | 9/2008 | Drew |
| 2008/0242961 A1 | 10/2008 | Brister et al. |
| 2008/0255438 A1 | 10/2008 | Saidara et al. |
| 2008/0262469 A1 | 10/2008 | Brister et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0300919 A1 | 12/2008 | Charlton et al. |
| 2008/0300920 A1 | 12/2008 | Brown et al. |
| 2008/0301158 A1 | 12/2008 | Brown et al. |
| 2008/0301665 A1 | 12/2008 | Charlton et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2009/0005666 A1 | 1/2009 | Shin et al. |
| 2009/0012379 A1 | 1/2009 | Goode et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0085768 A1 | 4/2009 | Patel et al. |
| 2009/0099436 A1 | 4/2009 | Brister et al. |
| 2009/0105554 A1 | 4/2009 | Stahmann et al. |
| 2009/0112478 A1 | 4/2009 | Mueller, Jr. et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0149717 A1 | 6/2009 | Brauer et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247931 A1 | 10/2009 | Damgaard-Sorensen |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |
| 2010/0190435 A1 | 7/2010 | Cook et al. |
| 2011/0004276 A1 | 1/2011 | Blair et al. |
| 2011/0152637 A1 | 6/2011 | Kateraas et al. |

(56) References Cited

U.S. PATENT DOCUMENTS

FOREIGN PATENT DOCUMENTS

| | | |
|---|---|---|
| CA | 2413148 | 8/2010 |
| DE | 4234553 | 1/1995 |
| EP | 0504835 | 5/1993 |
| EP | 0653718 | 1/1996 |
| EP | 0724859 | 8/1996 |
| EP | 0800082 | 12/1998 |
| EP | 0880936 | 3/1999 |
| EP | 0970655 | 1/2000 |
| EP | 0678308 | 5/2000 |
| EP | 1292218 | 3/2003 |
| EP | 1077634 | 7/2003 |
| EP | 1394758 | 3/2004 |
| EP | 1666091 | 6/2006 |
| EP | 1703697 | 9/2006 |
| EP | 1704893 | 9/2006 |
| EP | 1897487 | 11/2009 |
| EP | 1897492 | 11/2009 |
| EP | 2113864 | 11/2009 |
| EP | 1897488 | 12/2009 |
| EP | 1681992 | 4/2010 |
| EP | 1448489 | 8/2010 |
| EP | 1971396 | 8/2010 |
| EP | 2201969 | 3/2011 |
| GB | 1579690 | 11/1980 |
| GB | 2225637 | 6/1990 |
| JP | 2000-000231 | 1/2000 |
| JP | 2000-116628 | 4/2000 |
| WO | WO86/00513 | 1/1986 |
| WO | WO87/06040 | 10/1987 |
| WO | WO89/02246 | 3/1989 |
| WO | WO90/00367 | 1/1990 |
| WO | WO95/06240 | 3/1995 |
| WO | WO96/07908 | 3/1996 |
| WO | WO97/41421 | 4/1997 |
| WO | WO97/20207 | 6/1997 |
| WO | WO97/46868 | 6/1997 |
| WO | WO-97/33513 | 9/1997 |
| WO | WO98/09167 | 3/1998 |
| WO | WO98/24366 | 6/1998 |
| WO | WO98/52045 | 11/1998 |
| WO | WO99/05966 | 2/1999 |
| WO | WO99/32883 | 7/1999 |
| WO | WO00/13580 | 3/2000 |
| WO | WO00/20626 | 4/2000 |
| WO | WO00/33065 | 6/2000 |
| WO | WO00/78210 | 12/2000 |
| WO | WO01/24038 | 4/2001 |
| WO | WO01/33216 | 5/2001 |
| WO | WO01/52727 | 7/2001 |
| WO | WO01/57238 | 8/2001 |
| WO | WO01/57239 | 8/2001 |
| WO | WO01/67009 | 9/2001 |
| WO | WO02/078512 | 10/2002 |
| WO | WO03/105629 | 12/2003 |
| WO | WO2004/047445 | 6/2004 |
| WO | WO-2005/045744 | 5/2005 |
| WO | WO-2006/032653 | 3/2006 |
| WO | WO-2006/124099 | 11/2006 |
| WO | WO-2011/022418 | 2/2011 |

OTHER PUBLICATIONS

Canadian Patent Application No. 2,521,494, Examiner's Report mailed Dec. 8, 2011.
European Patent Application No. 04749713.6, Supplemental European Search Report, mailed Mar. 5, 2009.
European Patent Application No. 04749713.6, European Search Report, mailed Jul. 30, 2009.
Japanese Patent Application No. 2006-509676, English Translation of Office Action mailed Mar. 3, 2009.
PCT Application No. PCTUS20040 10338, International Search Report mailed Oct. 15, 2004.
PCT Application No. PCTUS20040 10338, International Preliminary Report on Patentability and Written Opinion of the International Searching Authority mailed Oct. 14. 2005.
U.S. Appl. No. 10/407,695, Office Action mailed Dec. 23, 2008.
U.S. Appl. No. 10/407,695, Office Action mailed Apr. 23, 2008.
U.S. Appl. No. 10/407,695, Office Action mailed Aug. 3, 2007.
U.S. Appl. No. 10/407,695, Office Action mailed Feb. 2, 2007.
U.S. Appl. No. 10/407,695, Office Action mailed Jun. 9, 2006.
U.S. Appl. No. 10/407,695, Office Action mailed Oct. 6, 2005.
U.S. Appl. No. 10/407,695, Notice of Allowance Jun. 5, 2009.
U.S. Appl. No. 10/407,695, Advisory Action Apr. 29, 2009.
U.S. Appl. No. 12/623,194, Office Action mailed Apr. 1, 2011.
U.S. Appl. No. 12/623,194, Office Action mailed Oct. 26, 2011.
U.S. Appl. No. 12/622,915, Office Action mailed Aug. 30, 2011.
U.S. Appl. No. 12/622,915, Office Action mailed Mar. 30, 2011.
U.S. Appl. No. 12/859,072, Office Action mailed Oct. 27, 2011.
U.S. Appl. No. 12/859,072, Office Action mailed Apr. 1, 2011.

* cited by examiner

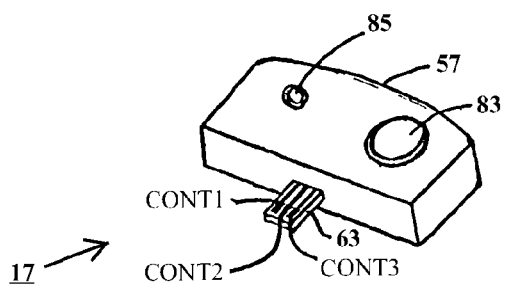
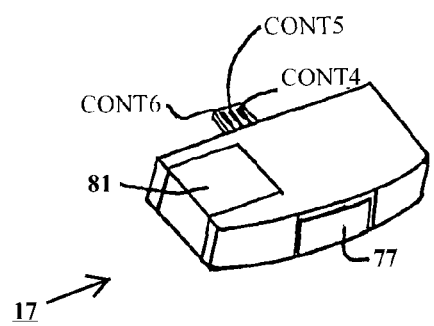
FIG. 6(a)  FIG. 6(b)
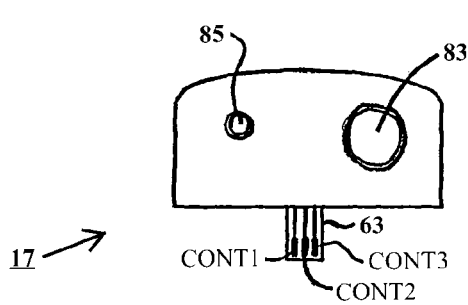
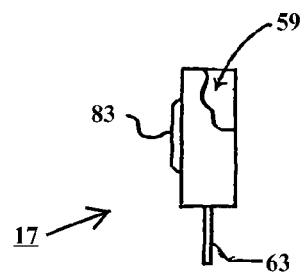
FIG. 6(c)  FIG. 6(d)

METHOD AND SYSTEM FOR TRANSFERRING ANALYTE TEST DATA

BACKGROUND OF THE INVENTION

The present invention relates generally to the field of analyte test instrument systems which can be used to perform electrochemical assays on biological samples. More particularly, the present invention relates to analyte test instrument systems which include an adaptor for transferring data stored on an analyte test instrument (e.g., a blood glucose monitor) to a data management device (e.g., a computer).

For many patients, the concentration of a particular analyte in blood must be routinely measured. The results of an analyte concentration measurement may, in turn, necessitate the patient to undertake a particular course of action in response thereto (e.g., requiring the patient to partake in a particular drug treatment).

Diabetes is a disease which typically requires a patient to routinely monitor the concentration of glucose in his/her blood. In particular, a patient suffering from diabetes is often required to measure the concentration of glucose in his/her blood multiple times each day. Based upon the results of each blood glucose measurement, the patient may require a particular drug treatment (e.g., an injection of insulin) in order to regulate that the blood glucose level of the patient remains within a specified range. Exceeding the upper limit of said range (hyperglycemia) or dropping beneath the lower limit of said range (hypoglycemia) should be avoided with as much diligence as possible to prevent the patient from experiencing serious medical complications which include, inter alia, retinopathy, nephropathy, and neuropathy.

Analyte test instrument systems are well known and are widely used in the art to perform routine electrochemical assays on biological samples. A blood glucose monitoring system is one well-known type of analyte test instrument system which is used to perform routine glucose concentration tests on blood samples.

One type of blood glucose monitoring system which is well known and widely used in the art comprises at least one disposable test strip which electrochemically reacts in response to the deposition of a blood sample thereon. The test strip is designed for use with a corresponding blood glucose monitor which calculates the concentration of blood glucose in the blood sample based upon the electrochemical reaction between the test strip and the blood sample. Examples of blood glucose monitoring systems of the type described above are manufactured and sold by Abbott Laboratories, Medisense Products of Bedford, Mass. under the PRECISION line of blood glucose monitoring systems.

A disposable, blood glucose monitoring test strip typically comprises a thin base, or substrate, layer which is generally rectangular in shape. A plurality of electrical contacts, or strips, are deposited along substantially the entire length of the base layer in a spaced apart, parallel relationship. One end of the electrical contacts is positioned within the reaction area of the test strip. In the reaction area of the test strip, an enzyme is deposited which is capable of reacting with the glucose in a blood sample to produce a measurable electrical response. The other end of the electrical contacts is disposed to electrically contact associated conductors located in the blood glucose monitor, as will be described further below.

A blood glucose monitor is typically modular and portable in construction to facilitate its frequent handling by the patient. A blood glucose monitor often comprises a multi-function test port which is adapted to receive the test strip in such a manner so that an electrical communication path is established therebetween. As such, an electrical reaction created by depositing a blood sample onto the reaction area of the test strip travels along at least one of the conductors of the test strip and into the test port of the blood glucose monitor. Within the housing of the monitor, the test port is electrically connected to a microprocessor which controls the basic operations of the monitor. The microprocessor, in turn, is electrically connected to a memory device which is capable of storing a multiplicity of blood glucose test results.

In use, a blood glucose monitor of the type described above can be used in the following manner to measure the glucose level of a blood sample and, in turn, store the result of said measurement into memory as test data. Specifically, a disposable test strip is inserted into the test port of the monitor. With the test strip properly inserted into the monitor, there is established a direct electrical contact between the conductors on the test strip and the conductors contained within the test port, thereby establishing an electrical communication path between the test strip and the monitor through which electrical signals can travel. Having properly disposed the test strip into the test port, the monitor typically displays a "ready" indication on its display.

The user is then required to deposit a blood sample onto the reaction area of the test strip, the acquisition of the blood sample typically being accomplished by pricking the fingertip of the patient with a lancing device. When a sufficient quantity of blood is deposited on the reaction area of the test strip, an electrochemical reaction occurs between the blood sample and the enzyme present in the reaction area which, in turn, produces an electrical current which decays exponentially over time.

The decaying electrical current created through the chemical reaction between the enzyme and the glucose molecules in the blood sample, in turn, travels along the electrically conductive path established between the test strip and the monitor and is measured by the microprocessor of the monitor. The microprocessor of the monitor; in turn, correlates the declining current to a standard numerical glucose value. The numerical glucose value calculated by the monitor is then shown on the monitor display for the patient to observe. In addition, the data associated with the particular blood glucose measurement is stored into the memory for the monitor.

It should be noted that blood glucose monitors of the type described above often include a memory device which is capable of storing a number of different events, wherein examples of some possible events include, but are not limited to, a blood glucose measurement, a calibration function, and a date/time change for the monitor. In fact, some blood glucose monitors are capable of storing in memory as many as 400 events at a single time.

In order to effectively monitor the blood glucose level patterns of a patient, a clinician and/or physician for a diabetes patient often downloads a series of blood glucose monitoring events onto a data management device, such as a computer, which is loaded with comprehensive data management system (DMS) software (e.g., the PRECISION LINK data management system software which is manufactured and sold by Abbott Laboratories, MediSense Products of Bedford, Mass.) capable of retrieving, managing and analyzing the data stored on the monitor. In particular, a clinical analyst and/or a physician for a diabetes patient is often interested in tracking the blood glucose levels of a patient over a fixed period of time (e.g., 1 month).

In order to effectively track the blood glucose levels of a patient over a fixed time, a clinical analyst and/or a physician is required to periodically meet with the patient and download all of the data stored in the blood glucose monitor into the data management device for comprehensive analysis. Analyzing the test results in this manner, the clinician and/or physician is able to assess how effectively the patient is able to regulate his/her blood glucose level.

Traditionally, the data stored on a blood glucose monitor is downloaded onto a data management device using a hardwire communication link. A hardwire communication link typically comprises a communication cable which, at one end, is provided with a test strip-shaped communication interface which can be removably inserted into the strip port of the blood glucose monitor and, at the other end, is provided with a connector which is adapted to removably connect with the serial port of a conventional computer.

As can be appreciated, a diabetes patient is somewhat limited in the frequency in which he/she can visit a clinician and/or physician to track glucose test results. As a result, diabetes patients are encouraged to frequently download the data stored on the blood glucose monitor onto his/her own computer for comprehensive analysis. In this manner, a diabetes patient can monitor his/her test results as frequently as desired (e.g., daily, weekly, etc.).

However, the process of electrically connecting a blood glucose monitor to a computer using a hardwire communication link has been found by some diabetes patients to be cumbersome, complicated, and time consuming. Overwhelmed by the connection process, some patients download their blood glucose levels onto a computer for further analysis less frequently than is desired, thereby increasing the patient's risk of experiencing a serious diabetes related medical complication, which is highly undesirable.

SUMMARY OF THE INVENTION

It is an object of the present invention to provide a method and system for wirelessly transferring analyte test data stored on an analyte test instrument, such as a blood glucose monitor, to a data management device, such as a computer.

It is another object of the present invention to provide a method and system for transferring analyte test data stored on an analyte test instrument to a data management device via an adaptor.

It is yet another object of the present invention to provide a method and system as described above wherein the adaptor can be removably connected to the analyte test instrument.

It is yet still another object of the present invention to provide a method and system as described above which has a limited number of parts, which is inexpensive to manufacture and which is easy to use.

Therefore, according to one feature of the present invention, there is provided a system for transferring data comprising an analyte test instrument which is adapted to store data, an adaptor removably connected to said analyte test instrument, said adaptor being in data communication with said analyte test instrument through a first data communication channel, and a data management device in data communication with said adaptor through a second data communication channel, said second communication channel being a wireless data communication channel.

According to another feature of the present invention, there is provided an adaptor for transferring data stored on an analyte test instrument to a wirelessly enabled data management device, said analyte test instrument comprising a data communication device, said adaptor comprising a data communication device, said data communication device for said adaptor being adapted to removably connect with the data communication device of said analyte test instrument so as to establish a first data communication channel between said adaptor and said analyte test instrument, a microcontroller in electrical connection with said data communication device for said adaptor, a wireless controller in electrical connection with said microcontroller, and a wireless transceiver in electrical connection with said wireless controller, said wireless transceiver being adapted to wirelessly communicate with said data management device through a second data communication channel.

According to another feature of the present invention, there is provided a method for transferring data stored on an analyte test instrument to a data management device via an adaptor, said adaptor being independent from said analyte test instrument, said method comprising the steps of removably connecting said adaptor to said analyte test instrument so as to establish a first data communication channel between said adaptor and said analyte test instrument, transferring data stored on said analyte test instrument to said adaptor through the first data communication channel, and transmitting the transferred data from said adaptor to said data management device through a second data communication channel, the second data communication channel being a wireless data communication channel.

Various other features and advantages will appear from the description to follow. In the description, reference is made to the accompanying drawings which form a part thereof, and in which is shown by way of illustration, various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts:

FIG. 6(a) is an enlarged, front perspective view of the adaptor shown in FIG. 1;

FIG. 6(b) is an enlarged, rear perspective view of the adaptor shown in FIG. 1;

FIG. 6(c) is an enlarged, front plan view of the adaptor shown in FIG. 1;

FIG. 6(d) is an enlarged, right side view, broken away in part, of the adaptor shown in FIG. 1;

DETAILED DESCRIPTION OF THE PREFERRED EMBODIMENT

Figure 1:
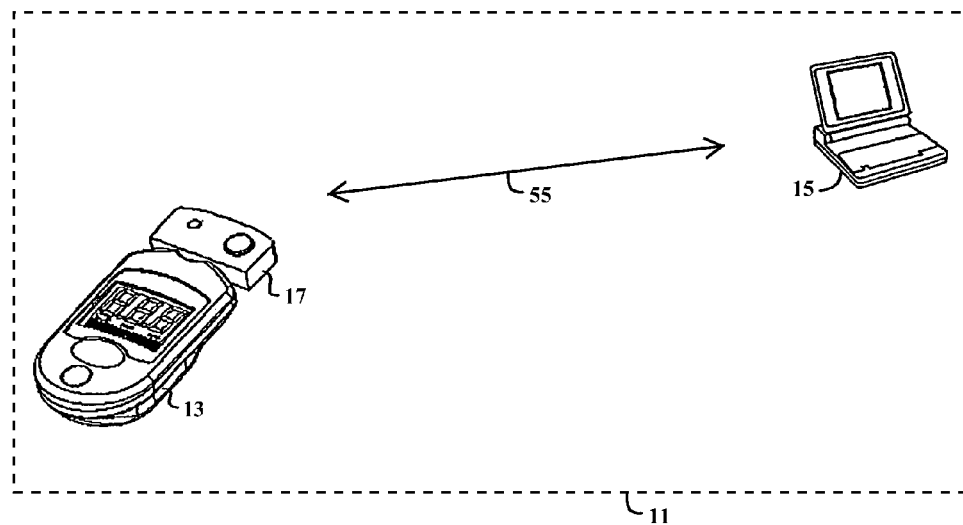
FIG. 1 is a perspective view of a first embodiment of a system for transferring analyte test data, said system being constructed according to the teachings of the present invention, the adaptor being shown connected to the analyte test instrument, the adaptor being shown in wireless communication with the data management device.
Figure 2:
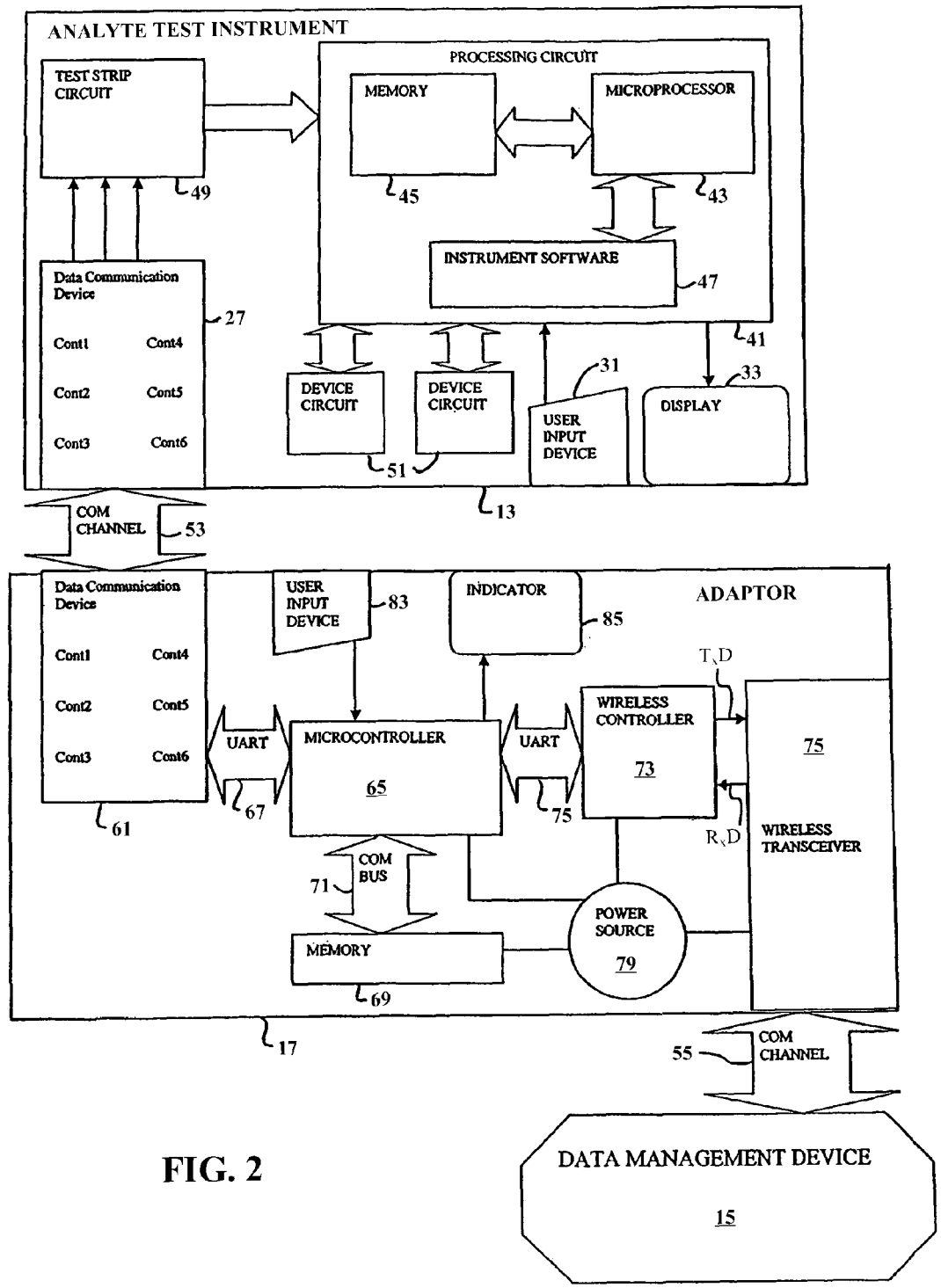
FIG. 2 is a simplified block diagram of the system shown in FIG. 1.

Referring now to FIGS. 1 and 2, there is shown a first embodiment of a system for transferring data, said system being constructed according to the teachings of the present invention and identified generally by reference numeral 11.

System 11 comprises an analyte test instrument (ATI) 13, a data management device (DMD) 15, and an adaptor 17. As will be described further in detail below, analyte test data stored in ATI 13 can be wirelessly transmitted to DMD 15 via adaptor 17.

Analyte test instrument 13 represents a monitor which can be used to measure the concentration of an analyte in a test sample. As is shown herein, ATI 13 is in the form of a conventional blood glucose monitor (e.g., an electrochemical or photometric blood glucose monitor). As such, ATI 13 is capable of measuring glucose concentrations of a blood sample and, in turn, storing the results of each blood glucose measurement as data in memory. As an example, ATI 13 may be of the type disclosed in U.S. Pat. No. 6,377,894 to Deweese et al, which is incorporated herein by reference.

ATI 13 is a communication enabled device. In this respect, ATI 13 is capable of serial data transfer with another device (e.g., adaptor 17), as will be described further in detail below.

Figure 3A:
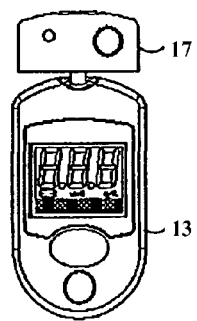
FIG. 3(a) is a front plan view of the analyte test instrument and the adaptor shown in FIG. 1, the adaptor being shown connected to the analyte test instrument.
Figure 3B:
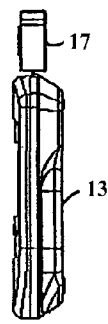
FIG. 3(b) is a right side view of the analyte test instrument and the adaptor shown in FIG. 1, the adaptor being shown connected to the analyte test instrument.
Figure 3C:
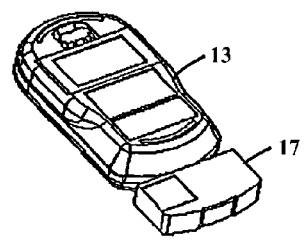
FIG. 3(c) is a rear perspective view of the analyte test instrument and the adaptor shown in FIG. 1, the adaptor being shown connected to the analyte test instrument.
Figure 4:
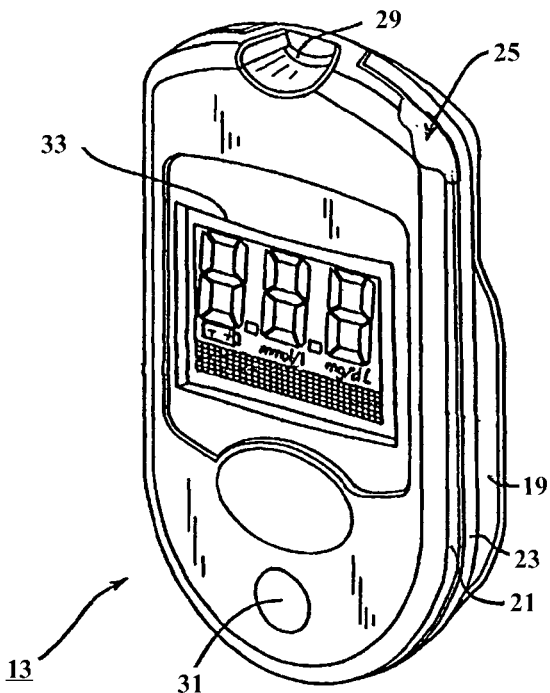
FIG. 4 is an enlarged front perspective view, broken away in part, of the analyte test instrument shown in FIG. 1.

Referring now to FIGS. 2-4, ATI 13 is a modular, self-contained, and portable unit which comprises a protective housing 19 constructed of a durable and inexpensive material, such as plastic. Housing 19 includes a front casing 21 and a rear casing 23 which are secured together by means of a snap-fit interconnection. With front casing 21 and rear casing 23 affixed together, housing 19 is a substantially enclosed device which is shaped to include an interior cavity 25 into which the electrical and electronic components of ATI 13 are disposed, as will be described further below.

ATI 13 comprises a data communication device 27 which is disposed within interior cavity 25 of housing 19 and which is accessible through a slot 29 formed into the top of housing 19. Data communication device 27 is a current source sensing device which is capable of transmitting and receiving serial data. In the present embodiment, data communication device 27 is in the form of a conventional multi-purpose test port which includes a slot shaped to matingly receive and electrically connect with, inter alia, a test strip, a calibration strip, or the interface connector of a hardwire communication link. Data communication device 27 comprises six metal contact strips, which are identified as contact strips Cont1 through Cont6 in FIG. 2.

It should be noted that data communication device 27 is not limited to a conventional multi-purpose test port. Rather, it is to be understood that data communication device 27 could be in the form of any conventional communication device which is capable of transmitting and receiving serial data without departing from the spirit of the present invention. As one example, data communication device 27 could alternatively be in the form of a wireless transceiver without departing from the spirit of the present invention. As another example, data communication device 27 could alternatively be in the form of a phone jack receptacle without departing from the spirit of the present invention, which will be described further in detail below.

ATI 13 also comprises a user input device 31 which is disposed within interior cavity 25 and which at least partially projects through an opening formed in front casing 21 of housing 19. User input device 31 is shown herein as being in the form of a button capable of being manually depressed. In use, input device 31 is for the manual regulation of a switch which, in turn, controls operative functions for ATI 13. In particular, input device 31 enables the user to regulate the power state of ATI 13, to recall information stored in memory, to respond to messages provided in the display, to provide access to menus generated by software contained within ATI 13, and to set some of the configuration control parameters.

Figure 5:
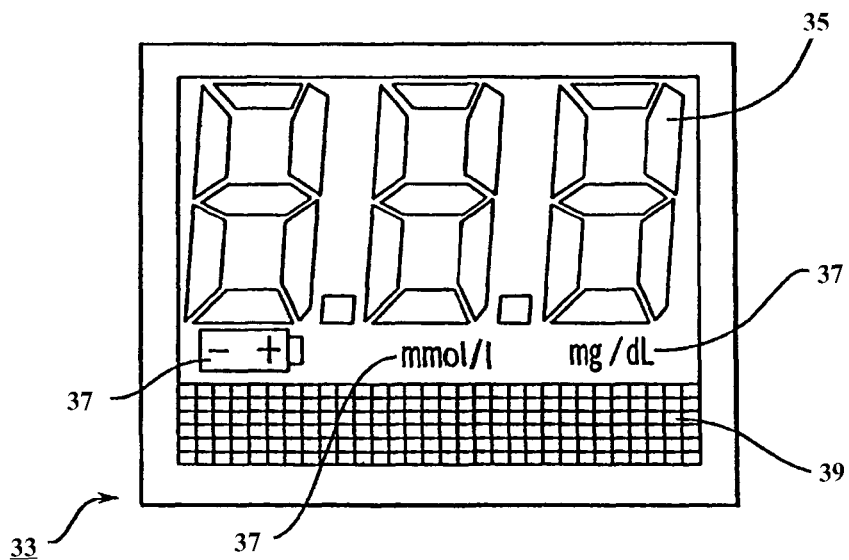
FIG. 5 is an enlarged front plan view of the display for the analyte test instrument shown in FIG. 1.

ATI 13 further comprises a display 33 which is disposed within interior cavity 25 and which is viewable through a transparent window formed in front casing 21 of housing 19. Display 33 is shown herein as being in the form of a screen designed to provide the user with information in a visual form. As can be seen most clearly in FIG. 5, display 33 is in the form of a liquid crystal display (LCD) which is used to display, inter alia, test results, user messages, and recalled information which is stored in the memory of ATI 13. Display 33 includes a numerical display 35 which is capable of generating three, seven-segment digital numbers. As can be appreciated, display 35 provides the user with a means for visually indicating the numerical value associated with a particular test result, display 35 including a pair of decimal point indicators to allow for a wider range of possible output values. Display 33 also comprises a plurality of icons 37 which indicate the units of measurement of a test result (e.g., mg/dL or mmol/l) and a low battery condition. Display 33 further comprises a dot-matrix message line 39 which can be used to provide information to the user, message line 39 being capable of generating up to 10 numerals or up to 9 characters at the same time. The information displayed by message line 39 can include, among other things, time and data information, user prompts (e.g., "apply blood"), error messages (e.g., "expired strip"), and configuration control settings (e.g., setting time or selecting a operating language).

It should be noted that the information shown on display 33 is controlled by display driver software for ATI 13. The display driver software provides display 33 with the ability to scroll a long message, flash a message or a portion of a message, or display alternating messages. In addition, the display driver software can provide ATI 13 with the ability to flash icons 37. Furthermore, as ATI 13 is powering up, the display driver software can support a visual check of display 33 wherein the icons and pixels for display 33 are turned on for a brief period to enable the user to confirm the entire display 33 is functioning properly.

ATI 13 preferably derives power from a power source (not shown) disposed within interior cavity 25. The power source may be in the form of one or more replaceable AA-type batteries which are removably mounted into an associated battery compartment in interior cavity 25 and which are accessible through a removable cover formed into rear casing 23 of housing 19. However, it is to be understood that any source of power capable of providing a suitable direct (DC) voltage can be used to provide power to ATI 13.

As seen most clearly in FIG. 2, user input 31 and display 33 are connected to a processing circuit 41 which, in turn, is connected to a microprocessor 43, memory 45, and instrument software 47. In addition, data communication device 27 is connected to processing circuit 41 through a test strip circuit 49.

Processing circuit 41 is an application specific integrated circuit (ASIC) which enables a test strip is inserted into direct electrical connection with data communication device 27 to communicate with microprocessor 43. For example, processing circuit 41 enables microprocessor 43 to send signals to data communication device 27 to determine the identity of a strip which is disposed into electrical connection therewith (i.e., to determine whether the strip is a calibration strip, a test strip, or the strip-like interface connector for a communication link). Microprocessor 43 may determine the identity of a strip disposed into electrical connection with data communication device 27 by measuring the impedance of said strip or by detecting the location of the electrical contacts on said strip.

Microprocessor 43 is an application specific integrated circuit (ASIC) that functions as the central processing unit for ATI 13. As such, microprocessor 43 performs the principal calculation and data management tasks for ATI 13.

Memory 45 is connected to microprocessor 43 and serves to retain data processed by microprocessor 43, said data being available for subsequent retrieval. Types of information that may be stored in memory 45 include measurement delay times, sample incubation times, number of measurements to be taken during an assay, thresholds against which voltage levels can be compared, values of excitation voltage levels applied to a test strip during assay, analyte value conversion factors, failsafe assay threshold values, and configurations of circuitry of analyte test instrument 13. It should be noted that memory 45 has the capacity to store a multiplicity of assay results. Specifically, each assay result is typically stored into memory 45 as a data bundle referred to herein as "an event". As can be appreciated, memory 45 is preferably of the type which can store in excess of 400 events.

Instrument software 47 is provided for microprocessor 43, software 47 functioning in response to information received at data communication device 27 from a calibration strip. Specifically, instrument software 47 uses the information received from a calibration strip to control the operation of the ATI 13. Instrument software 47 also controls operations of the ATI 13 that are independent of information introduced or generated at data communications device 27. For example, instrument software 47 enables the user to recall assay results and assay information, can provide various warning, error, and prompting messages, can permit setting of date and time, can control transmission of data to external devices, can monitor power level or battery level or both, and can provide indications to the user if power drops below a specified level.

A test strip circuit 49 connects data communication device 27 to processing circuit 41. In operation, test strip circuit 49 enables data to pass between data communication device 27 and processing circuit 41.

A pair of device circuits 51 are also connected to processing circuit 41. Device circuits 51 can comprise analog, digital, or mixed-signal circuits, application-specific integrated circuits (ASICs), and passive and active electrical components. Device circuits 51 can perform various electrical functions required by ATI 13. Specifically, device circuits 51 carry instructions from microprocessor 43 to various functional components of ATI 13 so that these components can perform their intended functions. As one example, device circuits 51 may serve to drive the clock functions for microprocessor 43.

In use, ATI 13 can be used in the following manner to measure and store analyte test data. Specifically, an analyte test strip is inserted into data communication device 27 so that the metal contacts on the test strip are in direct metal-to-metal contact with the contacts CONT1 through CONT6 of data communication device 27, thereby establishing a communication channel between the test strip and ATI 13. Having inserted the test strip into data communication device 27, instrument software 47 identifies the item inserted into data communication device 27 as an analyte test strip. At this time, microprocessor 43 executes software which generates a message on display 33 that notifies the user to deposit a sample onto the test strip. When a sample is deposited onto the reaction area of the test strip, the sample reacts with enzymes in the reaction area which, in turn, produces an electrical response in the form of a decaying electrical current. Test strip circuit 49 converts the decaying current from an analog signal to a digital signal and then passes the converted signal to processing circuit 41. The converted signal is then processed by microprocessor 43 to determine the analyte test value that corresponds to the signal. Microprocessor 43 then stores the analyte test data as an event in memory 45 and simultaneously registers the analyte test value on display 33 for the patient to read.

The aforementioned analyte testing process can be repeated as desired. As noted briefly above, each test performed is preferably stored into memory 45 as an event, memory 45 being capable of storing a large quantity of events which can be subsequently retrieved and analyzed by a personal computer using sophisticated data management software.

Although ATI 13 is represented herein as being in the form of a communication enabled, blood glucose monitor, it is to be understood that ATI 13 represents any conventional communication enabled device which can be used to measure the concentration of an analyte in a sample. As an example, ATI 13 may represent any of the PRECISION line of blood glucose monitors which are manufactured and sold by Abbott Laboratories, MediSense Products of Bedford, Mass.

Data management device (DMD) 15 is represented herein as being in the form of a wirelessly enabled, laptop computer. As such, DMD 15 is capable of serial data transfer with another device (e.g., adaptor 17) through a wireless communication channel.

Preferably, DMD 15 is provided with comprehensive data analysis software (e.g., the PRECISION LINK software manufactured and sold by Abbott Laboratories, MediSense Products of Bedford, Mass.) which allows for analyte test data stored on an analyte testing device (e.g., ATI 13) to be downloaded, managed, and analyzed (e.g., charted) by DMD 15, thereby providing the patient with sophisticated analyte test data monitoring and tracking capabilities, which is highly desirable.

Although DMD 15 is represented herein as being in the form of a wirelessly enabled, laptop computer, it is to be understood that DMD 15 is not limited to a wirelessly enabled laptop computer. Rather, DMD 15 could be in the form of other types of conventional, wirelessly enabled data management devices (e.g., desktop computer, personal data assistant (PDA), printer, etc.) without departing from the spirit of the present invention.

Adaptor 17 is a modular, self-contained and portable unit which can be removably connected to ATI 13, as seen most clearly in FIGS. 3(a)-(c). As will be described further in detail below, adaptor 17 is adapted to communicate with ATI 13 by means of a first communication channel 53 and wirelessly communicate with DMD 15 by means of a second communication channel 55. In this capacity, adaptor 17 can be used to retrieve data (e.g., analyte test data) stored in memory 45 via first communication channel 53 and, in turn, wirelessly transmit said data to DMD 15 via second communication channel 55.

As seen most clearly in FIGS. 2 and 6(a)-(d), adaptor 17 comprises a protective housing 57 constructed of a durable and inexpensive material, such as plastic. Housing 57 is a substantially enclosed device which is shaped to define an interior cavity 59 which is shaped to substantially receive the electrical and electronic components of adaptor 17, as will be described further below.

Adaptor 17 comprises a data communication device 61 disposed within interior cavity 59 and which partially and fittingly protrudes out through a narrow slot formed in the bottom of housing 57. Data communication device 61 is a communication device which is capable of electrically connecting with data connection device 27 of ATI 13, so as to establish communication channel 53 between ATI 13 and adaptor 17 through which data can be transmitted and received.

In the present embodiment, the portion of data communication device 61 which extends out from housing 57 is in is in the form of a rectangular strip 63 having the same approximate width and thickness as a test strip used in conjunction with data communication device 27. Six metal contact strips, which are identified as contact strips Cont1 through Cont6 in FIGS. 2 and 6(a)-(c), are deposited along substantially the entire length of strip 63 in a spaced apart, parallel relationship. As such, when strip 63 of data communication device 61 is inserted into the test port configuration of data communication device 27, each of the contact strips, or leads, on data communication device 61 is disposed in direct conductive contact with an associated contact strip within the test port. In this manner, with data communication device 61 properly inserted into the test port slot for data communication device 27, communication channel 53 is established between ATI 13 and adaptor 17 through which serial data is capable of being transferred.

It should be noted that the particular construction of data communication device 61 enables adaptor 17 to be removably connected to ATI 13. As a result, adaptor 17 can be manufactured and stored separately from ATI 13, adaptor 17 being connected to ATI 13 to form communication channel 53 only when the user desires to send data from ATI 13 to DMD 15.

As can be appreciated, the ability to removably connect adaptor 17 to ATI 13 provides the user with a number of significant advantages. As a first advantage, when the user only desires to store data onto ATI 13 and is not interested in wirelessly transmitting said data to DMD 15, adaptor 17 can be separated from ATI 13, thereby reducing the overall size and weight of the unit, which is highly desirable. As a second advantage, the particular construction of data communication device 61 enables adaptor 17 to be used in conjunction with many types of pre-existing types of analyte test instruments. As a result, a patient who owns a pre-existing ATI which is compatible with adaptor 17 can wirelessly transmit data stored on said pre-existing ATI to a data management device, such as a computer, simply by purchasing adaptor 17, which is highly desirable.

It should be noted that data communication device 61 is not limited to the test strip-type configuration shown herein. Rather, it is to be understood that data communication device 61 could be in the form of alternative types of conventional communication devices which are capable of transmitting and receiving serial data without departing from the spirit of the present invention. Specifically, data communication device 27 and data communication device 61 represent any compatible means for establishing a communication channel (e.g., wireless, hardwire) therebetween. As will be described further in detail below, data communication device 61 may be in the form of a male, phone jack and data communication device 27 may be in the form of a female, phone jack receptacle without departing from the spirit of the present invention.

Data communication device 61 is electrically connected to a microcontroller 65 via universal asynchronous receiver transmitter (UART) communication bus 67, microcontroller 65 being disposed within interior cavity 59 of housing 57. Microcontroller 65 is an application specific integrated circuit (ASIC) which functions as the central processing unit for adaptor 17. As such, microcontroller 65 is responsible for, inter alia, the processing and managing of data which is retrieved from ATI 13 and wirelessly transmitted to DMD 15, as will be described further in detail below.

For purposes of the present specification and claims, the term microcontroller shall mean microcontroller or microprocessor unless otherwise specified.

Memory 69 is disposed within interior cavity 59 of housing 57 and is electrically connected to microcontroller 65 through a communication bus 71. As will be described further below, memory 69 serves two principal functions. As a first function, memory 69 stores the application code software for adaptor 17. As a second function, memory 69 temporarily stores (i.e., buffers) the data retrieved from ATI 13 prior to its transmission to DMD 15. It should be noted that memory 69 preferably includes two separate memory devices, one of said memory devices being responsible for storing the application code software for adaptor 17 and the other of said memory device being responsible for temporarily storing the data retrieved from ATI 13 prior to its transmission to DMD 15.

A wireless controller 73 is disposed within interior cavity 59 of housing 57 and is electrically connected to microcontroller 65 via universal asynchronous receiver transmitter (UART) communication bus 75. As will be described further in detail below, in response to commands sent by micronroller 65, wireless controller 73 serves to regulate the operation of a wireless transceiver 75.

For purposes of the present specification and claims, wireless controller 73 represents both a component which is physically separate from microcontroller 65 as well as a component which is physically incorporated into microcontroller 65 to form an integrated device unless otherwise specified.

Wireless transceiver 75 is disposed within interior cavity 59 of housing 57 and is electrically is connected to wireless controller 73 via a transmitter line TxD and a receiver line RxD, electrical signals passing from controller 73 to transceiver 75 traveling via transmitter line TxD and electrical signals passing from transceiver 75 to controller 73 traveling via receiver line RxD. As will be described further in detail below, wireless transceiver 75 serves to transmit electrical signals to DMD 15 and receive electrical signals from DMD 15. Preferably, wireless transceiver 75 is disposed within interior cavity 59 in close proximity to a window 77 formed into the top of housing 17 through which signals are capable of traveling.

It should be noted that wireless transceiver 75 represents any conventional transceiver which is capable of two-way communication with a communication enabled device. As a result, wireless communication channel 55 represents any conventional two-way wireless communication channel (e.g., infrared (IR), such as infrared data (IrDA), or radio frequency (RF), such as Bluetooth, 802.11, Zigbee).

A power source 79 is disposed within interior cavity 59 of housing 57 and is electrically connected to microcontroller 65, memory 69, wireless controller 73 and wireless transceiver 75. Power source 79 is preferably in the form of a replaceable 3 volt, coin cell lithium battery which is accessible through a door 81 which is slidably mounted onto housing 57. However, it is to be understood that power source 79 is not limited to a 3 volt, coin cell lithium battery. Rather, it is to be understood that power source 79 could be in the form of additional types of conventional power sources (e.g., a solar battery cell) without departing from the spirit of the present invention. In addition, it is to be understood that power source 79 could be eliminated entirely from adaptor 17 without departing from the spirit of the present invention. Specifically, if power source 79 were to be removed from adaptor 17, power could alternatively be supplied to adaptor 17 from the power source of ATI 13.

A user input device 83 is disposed within interior cavity 59 and is sized and shaped to fittingly project through a corresponding opening formed in the front of housing 57. User input device 83 is preferably in the form of a circular button which can be manually depressed so as to selectively close a switch which is electrically connected to microcontroller 65. As will be described further below, input device 83 serves as a finger actuable means for triggering the execution of the data transfer from adaptor 17 to DMD 15.

An indicator 85 is disposed within interior cavity 59 and is sized and shaped to fittingly project through a corresponding opening formed in the front of housing 57. Indicator 85 is preferably in is in the form of a green light emitting diode (LED) which is electrically connected to microcontroller 65. As will be described further in detail below, indicator 85 serves as a means for providing the user with a visual indication of the operating state of indicator (e.g., whether indicator 85 is transferring data to DMD 15).

As noted above, system 11 is capable of transferring data stored in memory 45 of ATI 13 to DMD 15 via adaptor 17. As will be described further below, system 11 transfers data stored on ATI 13 to DMD 15 via adaptor 17 by means of a two-step process. In the first step of the two step process, data stored in memory 45 of ATI 13 is transferred into buffer memory 69 of adaptor 17. In the second step of the two step process, data transferred into buffer memory 69 of adaptor 17 is, in turn, wirelessly transmitted to DMD 15. Each of the two aforementioned steps will be discussed further in detail below.

Figure 7:
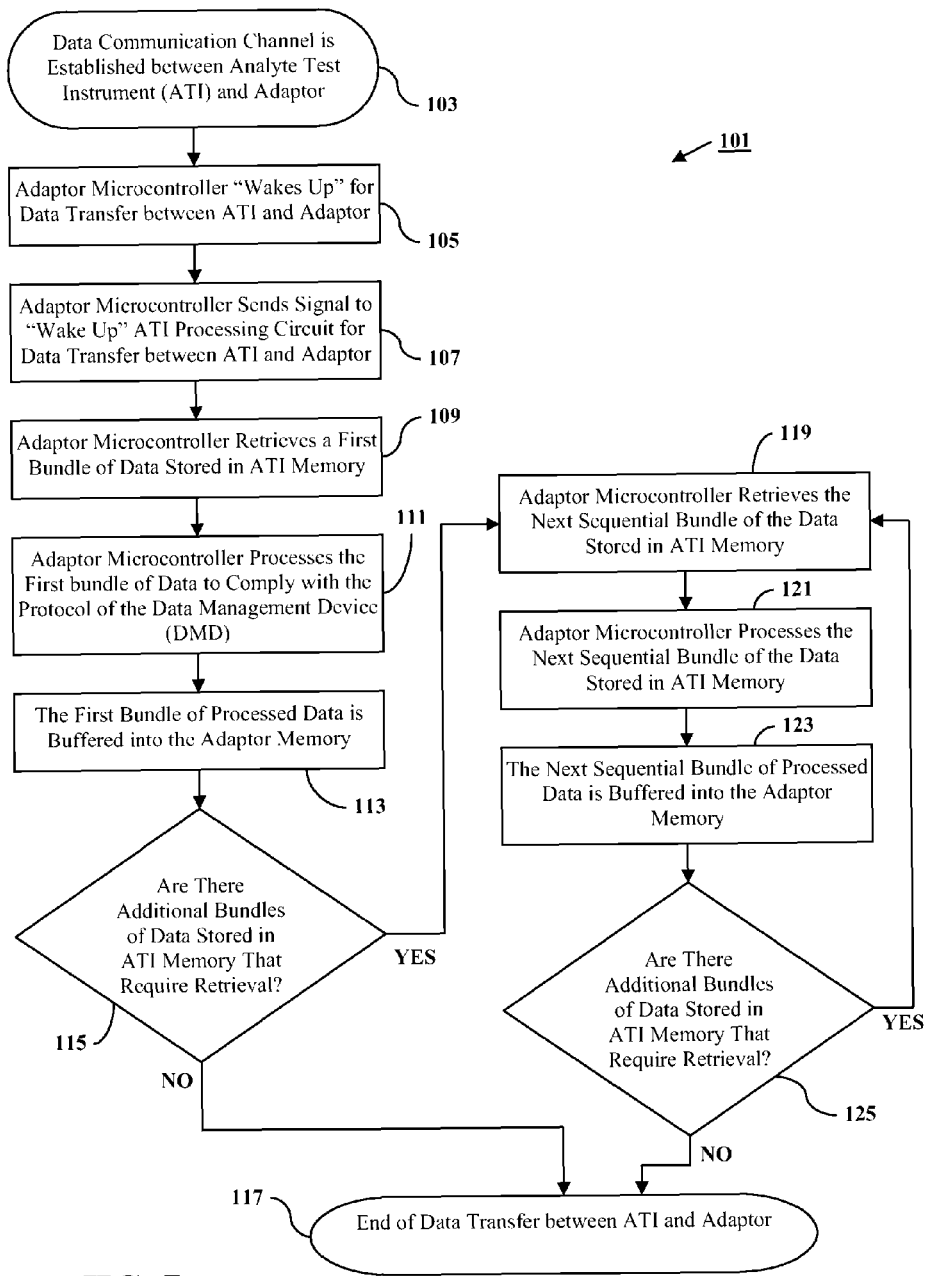
FIG. 7 is a flow chart depicting the method in which the system shown in FIG. 1 transfers data from the analyte test instrument to the adaptor.

FIG. 7 is a flow chart illustrating the method in which system 11 transfers data from ATI 13 to adaptor 17, said method being represented generally by reference numeral 101. Method 101 commences once data communication channel 53 is established between ATI 13 and adaptor 17, said step being represented by reference numeral 103. It should be noted that, for system 11, data communication channel 53 is established between ATI 13 and adaptor 17 by inserting strip 63 of data communication device 61 into the corresponding test port slot of data communication device 27, wherein the electrical conductors on data communication device 61 are disposed in direct electrical contact against the electrical conductors within data communication device 27.

Having established data communication channel 53 between ATI 13 and adaptor 17 in step 103, adaptor microcontroller 65 becomes active, or "wakes up", in anticipation of the transfer of data between ATI 13 and adaptor 17, said step being represented by reference numeral 105. Specifically, once data communication channel 53 has been established between ATI 13 and adaptor 17, the protocol for ATI 13 is to send out a signal to determine the type of device (e.g., adaptor, analyte test strip, calibration test strip) connected to data communication device 27. It is this signal sent by ATI 13 to determine the type of device connected to data communication device 27 which, in turn, serves to activate adaptor microcontroller 65. Once adaptor microcontroller 65 becomes active, adaptor microcontroller 65 then sends a signal to activate, or "wake up", microprocessor 43 for ATI 13 in anticipation of data transfer between ATI 13 and adaptor 17, said step being represented by reference numeral 107.

With adaptor microcontroller 65 and ATI microprocessor 43 having been activated in steps 105 and 107, adaptor microcontroller 65 receives a first bundle of data stored in memory 45 of ATI 13, said step being represented by reference numeral 109. It should be noted that adaptor microcontroller 65 is programmed to understand the protocol of ATI 13 (e.g., ASTM 1381 protocol) and, as a result, can recognize the particular bundles, or packets, of data stored in memory 45 of ATI 13. Having received the first bundle of data in step 109, adaptor microcontroller 65 processes (i.e., reformats and sorts) the first bundle of data in order to render said bundle in compliance with the data receiving protocol for DMD 15, said step being represented by reference numeral 111. In step 113, the first bundle of processed data in microcontroller 65 is then buffered into memory 69.

Having completed the transfer of the first bundle of data from memory 45 of ATI 13 to buffer memory 69 of adaptor 17, microcontroller 65 then sends a signal to microprocessor 43 to determine whether additional bundles of data remain in memory 45 for ATI 13 that need to be retrieved by adaptor 17, said step being represented by reference numeral 115. If there are no additional bundles of data located in memory 45 of ATI 13, the data transfer process between ATI 13 and adaptor 17 ends, as represented by reference numeral 117.

However, if additional bundles of data are located in memory 45 of ATI 13, adaptor microcontroller 65 receives the next sequential bundle of data stored in memory 45 of ATI 13, said step being represented by reference numeral 119. Having received the next sequential bundle of data in step 119, adaptor microcontroller 65 processes said bundle of data in step 121. In step 123, said bundle of processed data in microcontroller 65 is then buffered into memory 69.

Having completed the transfer of the next sequential bundle of data from ATI 13 to adaptor 17, microcontroller 65 then sends an additional signal to microprocessor 43 to determine whether more bundles of data remain in memory 45 of ATI 13 that need to be retrieved by adaptor 17, said step being represented by reference numeral 125. If there are no additional bundles of data located in memory 45, method 101 proceeds to step 117. However, if additional bundles of data are located in memory 45 of ATI 13, method 101 returns to step 119. As such, method 101 continues until all the bundles of data in memory 45 for ATI 13 are properly transferred into memory 69 for adaptor 17.

Figure 8:
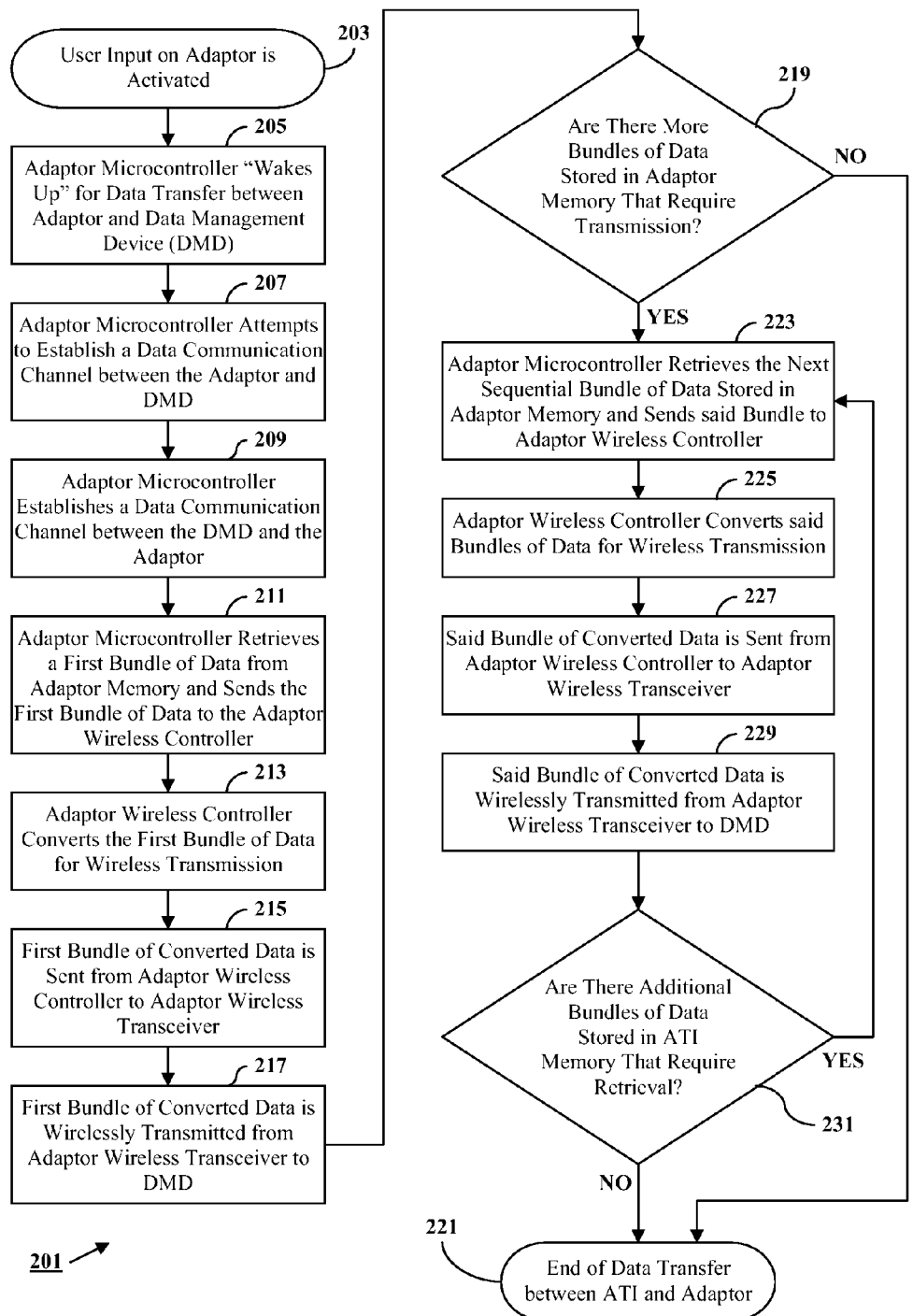
FIG. 8 is a flow chart depicting the method in which the system shown in FIG. 1 wirelessly transmits data from the adaptor to the data management device.

Having completed the first step of the two-step process for transferring data from ATI 13 to DMD 15 via adaptor 17, system 11 is now prepared to execute the second step of the two-step process for transferring data from ATI 13 to DMD 15 via adaptor 17. More specifically, system 11 is now prepared to wirelessly transmit the data buffered into memory 69 of adaptor 17 to wirelessly enabled DMD 15. FIG. 8 is a flow chart illustrating the method by which system 11 transfers data from memory 69 of adaptor 17 to DMD 15, said method being represented generally by reference numeral 201.

Method 201 commences once user input device 83 on adaptor 17 is activated (i.e., depressed), said step being represented by reference numeral 203. The activation of user input device 83 in step 203, causes adaptor microcontroller 65 to become active, or "wake up", in anticipation of data transfer between adaptor 17 and DMD 15, said step being represented by reference numeral 205.

Once activated, adaptor microcontroller 65 instructs wireless controller 73 to have wireless transceiver 75 send out a signal through window 77 in order to establish a data communication channel 55 between adaptor 17 and DMD 15, said step being represented by reference numeral 207. It should be noted that during step 207, adaptor microcontroller 65 simultaneously instructs indicator 85 to provide a signal (e.g., a flashing green light) to notify the user of the attempt by adaptor 17 to establish a data communication channel 55 with DMD 15. If compatible, adaptor 17 and DMD 15 will be able to establish data communication channel 55, said step being represented by reference numeral 209. It should be noted that, upon establishing data communication channel 55 between adaptor 17 and DMD 15, adaptor microcontroller 65 simultaneously instructs indicator 85 to provide a signal (e.g., a solid, non-flashing green light) to notify the user of the established data communication channel.

With data communication channel 55 having been established between adaptor 17 and DMD 15, adaptor microcontroller 65 retrieves a first bundle of data from adaptor memory 69 and, in turn, sends said first bundle of data to wireless controller 73, as represented by reference numeral 211. It should be noted that the size of the first data bundle retrieved from adaptor memory 69 is dependent upon the transfer protocol established between adaptor 17 and DMD 15. In step 213, wireless controller 73 coverts the first bundle of received data into a format suitable for wireless transmission. The converted first bundle of data is then sent from wireless controller 73 to wireless transceiver 75 through transmission line TxD, said step being represented by reference numeral 215. In step 217, the converted first bundle of data is wirelessly transmitted from wireless transceiver 75 to DMD 15.

Having completed the transfer of the first bundle of data from adaptor 17 to DMD 15, microcontroller 65 then sends out a signal to determine whether additional data bundles remain in adaptor memory 69, said step being represented by reference numeral 219. If there are no additional bundles of data located in memory 69, the data transfer process between adaptor 17 and DMD 15 terminates, as represented by reference numeral 221. It should be noted that once method 201 reaches step 221, adaptor microcontroller 65 simultaneously turns off indicator 85 to notify the user that the transfer of data between adaptor 17 and DMD 15 has completed.

However, if additional bundles of data are located in memory 69, adaptor microcontroller 65 retrieves the next sequential bundle of data from adaptor memory 69 and, in turn, forwards said bundle to wireless controller 73, as represented by reference numeral 223. In step 225, wireless controller 73 coverts the next sequential bundle of received data into a format suitable for wireless transmission. The converted bundle of data is then sent from wireless controller 73 to wireless transceiver 75 through transmission line TxD, said step being represented by reference numeral 227. In step 229, the converted bundle of data is wirelessly transmitted from wireless transceiver 75 to wireless enabled DMD 15.

Having completed the transfer of the next sequential bundle of data from adaptor 17 to DMD 15, microcontroller 65 then sends an additional signal to determine whether more bundles of data remain in memory 69 for adaptor 17, said step being represented by reference numeral 231. If there are no additional bundles located in adaptor memory 69, method 201 proceeds to step 221. However, if additional bundles of data are located in adaptor memory 69, method 201 returns to step 223. As such, method 201 continues until all of the bundles of data stored in adaptor memory 69 are wirelessly transmitted to DMD 15.

As noted above, data communication device 61 of adaptor 17 is preferably in the form of a strip-type connective interface which includes multiple metal contacts and communication device 27 is preferably in the form of a slotted, multi-purpose test port which includes multiple metal contacts. Preferably, the strip-type connective interface of device 27 is sized and shaped to be fittingly inserted into the slot of the multi-purpose test port of device 61 so that the metal contacts of device 61 are disposed in direct electrical contact with the metal contacts within device 27. In this manner, data communication channel 53 is established between ATI 13 and adaptor 17.

However, it is to be understood that system 11 is not limited to the particular type of electrical interconnection between ATI 13 and adaptor 17 as described above. In particular, system 11 is not limited to data communication device 61 being in the form of a strip-type connective interface with multiple metal contacts and data communication device 27 being in the form of a multi-purpose test port with multiple metal contacts. Rather, it is to be understood that data communication devices 27 and 61 are meant to represent any complementary pair of connectors which can be removably interconnected so as to establish a serial data communication channel therebetween.

Figure 9:
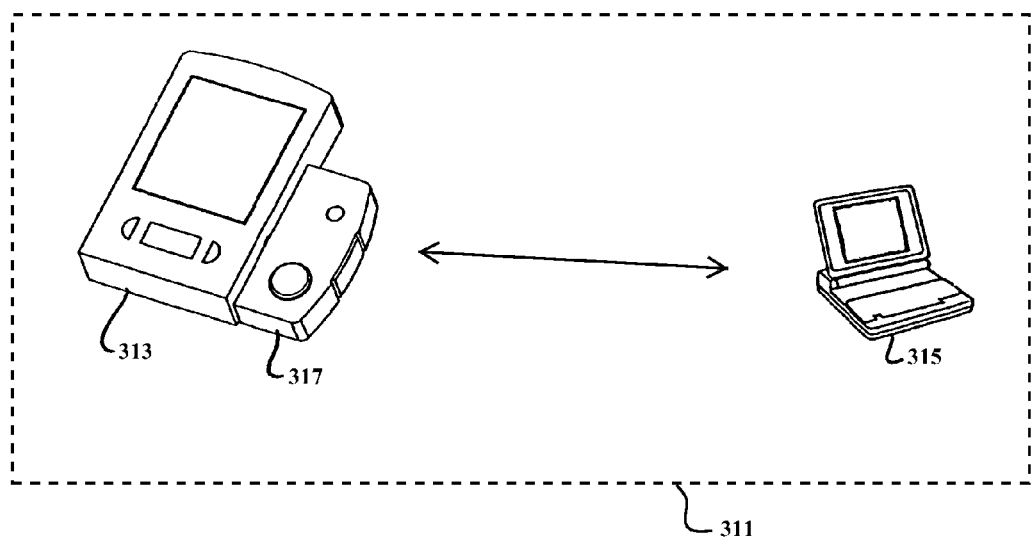
FIG. 9 is a perspective view of a second embodiment of a system for transferring analyte test data, said system being constructed according to the teachings of the present invention, the adaptor being shown connected to the analyte test instrument, the adaptor being shown in wireless communication with the data management device.
Figure 10:
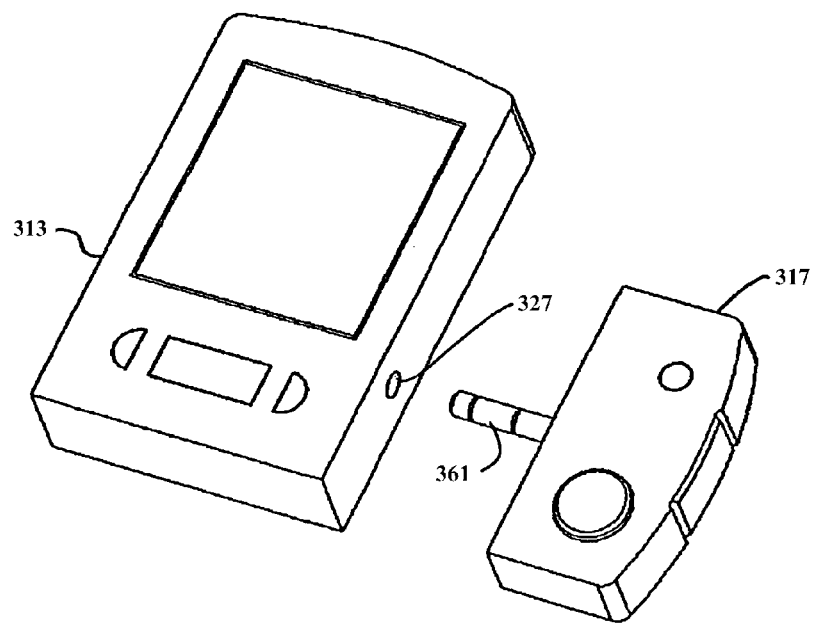
FIG. 10 is an enlarged front perspective view of the analyte test instrument and the adaptor shown in FIG. 9, the adaptor being shown disconnected from the analyte test instrument.

As an example, referring now to FIG. 9, there is shown a second embodiment of a system for transferring data, said system being constructed according to the teachings of the present invention and identified generally by reference numeral 311.

System 311 is similar to system 11 in that system 311 comprises an analyte test instrument (ATI) 313, a data management device (DMD) 315 and an adaptor 317, wherein analyte test data stored in ATI 313 can be wirelessly transmitted to DMD 315 via adaptor 317.

The principal distinction between system 311 and system 11 lies in the fact that adaptor 317 releasably interconnects with ATI 313 in a different manner in which adaptor 17 releasably interconnects with ATI 13. Specifically, ATI 313 comprises a data communication device 327 which is in the form of a conventional, female-type, conductive phone jack receptacle and adaptor 317 comprises a data communication device 361 which is in the form of conventional, male-type, conductive phone jack. Preferably, the phone jack receptacle of device 327 is sized and shaped to fittingly and releasably receive the phone jack of device 361, with device 361 being disposed in direct electrical contact with device 327. As such, a serial data communication path can be established between adaptor 317 and ATI 313, which is highly desirable.

It should be noted that the adaptors of the present invention which were described in detail above can be used in conjunction with various types of analyte test instruments. By providing adaptors which can be used with different types of analyte test instruments, the present invention serves to create a standardized means for wirelessly transmitting data of any format from any type of analyte test instrument to a common data management device, which is highly desirable.

The embodiments shown in the present invention are intended to be merely exemplary and those skilled in the art shall be able to make numerous variations and modifications to it without departing from the spirit of the present invention.

All such variations and modifications are intended to be within the scope of the present invention as defined in the appended claims.

What is claimed is:

1. An analyte test instrument, comprising:
a housing;
a test strip port disposed in the housing and sized to receive an analyte test strip;
a processor disposed in the housing;
a power source disposed in the housing and electrically coupled to the processor and the test strip port; and
memory operably coupled to the processor, wherein the memory includes instructions stored therein for execution by the processor, the instructions comprising:
instructions for receiving an indication that a test strip is inserted into the test strip port;
instructions for performing an analyte test measurement when a sample is applied to the test strip;
instructions for storing analyte test data from the analyte test measurement;
instructions for receiving an indication that an adaptor is removably connected to the test strip port;
instructions for providing power to the adaptor and to a wireless transceiver in the adaptor to enable wireless transmission of the stored analyte test data;
instructions for establishing a communication channel with the adaptor through the test strip port; and
instruction for transferring the stored analyte test data from the analyte test instrument to the adaptor through the test strip port.

2. The analyte test instrument of claim 1, wherein the analyte test data is transferred in a first bundle of data.

3. The analyte test instrument of claim 2, wherein the instructions comprise instructions for transferring additional bundles of data.

4. The analyte test instrument of claim 1, wherein the analyte is glucose.

5. The analyte test instrument of claim 1, wherein the analyte test instrument further comprises a display configured to provide a user of the analyte test instrument with information in a visual form.

6. The analyte test instrument of claim 5, wherein the information comprises analyte concentration data.

7. The analyte test instrument of claim 5, wherein the display is a liquid crystal display (LCD).

8. The analyte test instrument of claim 5, wherein the display comprises a numerical display.

9. The analyte test instrument of claim 5, wherein the display comprises a dot-matrix message line configured to provide information to the user.

10. The analyte test instrument of claim 5, wherein the display is configured to display a warning or prompting message to the user.

11. The analyte test instrument of claim 1, wherein analyte test data from a plurality of analyte test measurements are stored.

12. The analyte test instrument of claim 11, wherein the device further comprises a user input device.

13. The analyte test instrument of claim 12, wherein the user input device is configured to allow a user of the device to recall the stored analyte test data.

14. An adaptor, comprising:
a housing;
a connector strip adapted to removably connect to a test strip port in an analyte test instrument, wherein the test strip port is an analyte test strip port that receives analyte test strips;
a processor disposed in the housing;
a wireless transceiver disposed in the housing and operably coupled to the processor;
wherein the adaptor is configured to receive power for the processor and the wireless transceiver through the test strip port from the anlayte test instrument when connected; and
memory operably coupled to the processor, wherein the memory includes instructions stored therein for execution by the processor, the instructions comprising:
instructions for receiving an indication that the adaptor is removably connected to the test strip port of the analyte test instrument;
instructions for powering the wireless transceiver to enable wireless transmission of the stored analyte test data;
instructions for establishing a communication channel with the analyte test instrument through the test strip port; and
instructions for receiving analyte test data transferred from the analyte test instrument to the adaptor through the test strip port; and
instructions for wirelessly transmitting the analyte test data via the wireless transceiver to a data management device configured to analyze the analyte test data.

15. The adaptor of claim 14, wherein the instructions comprise instructions for providing a visual indication on the adaptor, the visual indication to indicate to a user that the analyte test data is being wirelessly transmitted.

16. The adaptor of claim 14, wherein the adaptor is configured to utilize infrared (IR) or radio frequency (RF) communication to wirelessly transmit the analyte test data to the data management device.

17. The adaptor of claim 15, wherein the adaptor is configured to utilize IR communication, and wherein the IR communication is infrared data (IrDA) communication.

18. The adaptor of claim 14, wherein the instructions comprise:
instructions for receiving communications from the data management device.

19. The adaptor of claim 14, wherein the data management device is one selected from a laptop computer, a desktop computer, and a personal digital assistant (PDA).

20. The adaptor of claim 14, comprising an input device, wherein the instructions comprise instructions for wirelessly transmitting the analyte test data to the data management device after receiving an indication that the input device is actuated.

21. The adaptor of claim 14, wherein the instructions comprise instructions for receiving the analyte test data in a first bundle of data via the test strip port of the analyte test instrument.

22. The adaptor of claim 21, wherein the instructions comprise:
instructions for sending a signal to the analyte test instrument via the test strip port to determine whether additional bundles of data remain; and
instructions for receiving the additional bundles of data via the test strip port of the analyte test instrument.

23. The adaptor of claim 14, wherein the instructions comprise instructions for storing the analyte test data after the analyte test data is received by the adaptor via the test strip port of the analyte test instrument.

24. The adaptor of claim 14, wherein the analyte is glucose.

* * * * *